(12) United States Patent
Anikeeva et al.

(10) Patent No.: US 9,681,979 B2
(45) Date of Patent: Jun. 20, 2017

(54) INDEPENDENT MAGNETICALLY-MULTIPLEXED HEATING OF PORTIONS OF A TARGET

(71) Applicant: MASSACHUSETTS INSTITUTE OF TECHNOLOGY, Cambridge, MA (US)

(72) Inventors: Polina Olegovna Anikeeva, Sommerville, MA (US); Ritchie Chen, Cambridge, MA (US); Michael Gary Christiansen, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 364 days.

(21) Appl. No.: 14/556,787

(22) Filed: Dec. 1, 2014

(65) Prior Publication Data

US 2015/0150714 A1 Jun. 4, 2015

Related U.S. Application Data

(60) Provisional application No. 61/910,395, filed on Dec. 1, 2013.

(51) Int. Cl.
| | | |
|---|---|---|
| *A61F 7/00* | (2006.01) |
| *A61N 1/40* | (2006.01) |
| *A61N 2/00* | (2006.01) |
| *A61N 2/02* | (2006.01) |

(52) U.S. Cl.
CPC ............... *A61F 7/00* (2013.01); *A61N 1/406* (2013.01); *A61N 2/002* (2013.01); *A61N 2/004* (2013.01); *A61N 2/02* (2013.01); *A61F 2007/009* (2013.01)

(58) Field of Classification Search
CPC ....... A61F 7/00; A61F 2007/009; A61N 2/02; A61N 2/002; A61N 2/004; A61N 1/406
See application file for complete search history.

(56) References Cited

U.S. PATENT DOCUMENTS

| | | | | |
|---|---|---|---|---|
| 2006/0246143 A1* | 11/2006 | Ege | ..................... | A61B 18/04 424/489 |
| 2007/0148437 A1* | 6/2007 | Muller-Schulte | .... | A61K 9/0009 428/327 |
| 2007/0164250 A1* | 7/2007 | Hamad-Schifferli | ........... | A61K 41/0052 252/62.51 C |

* cited by examiner

*Primary Examiner* — Christine H Matthews
*Assistant Examiner* — Joshua D Lannu
(74) *Attorney, Agent, or Firm* — Yakov Sidorin; Quarles & Brady LLP

(57) ABSTRACT

A predetermined spatial locale is selectively operationally stimulated through local heating by exposing magnetic particle(s) associated with such local to alternating magnetic field parameters of which are chosen to generate hysteretic losses in magnetic particle(s). When different types of particles are associated with different locales such as different biological cells, different cells can be accessed and stimulated independently from one another. Switching between stimulation of first and second types of cells is carried out by changing parameters of stimulating magnetic field, while optionally maintaining the field strength-frequency product substantially constant. Embodiments facilitate multiplexed release of chemical payloads, triggering changes in electrical polarization, and changing a shape of a unit placed at the chosen locale.

9 Claims, 14 Drawing Sheets

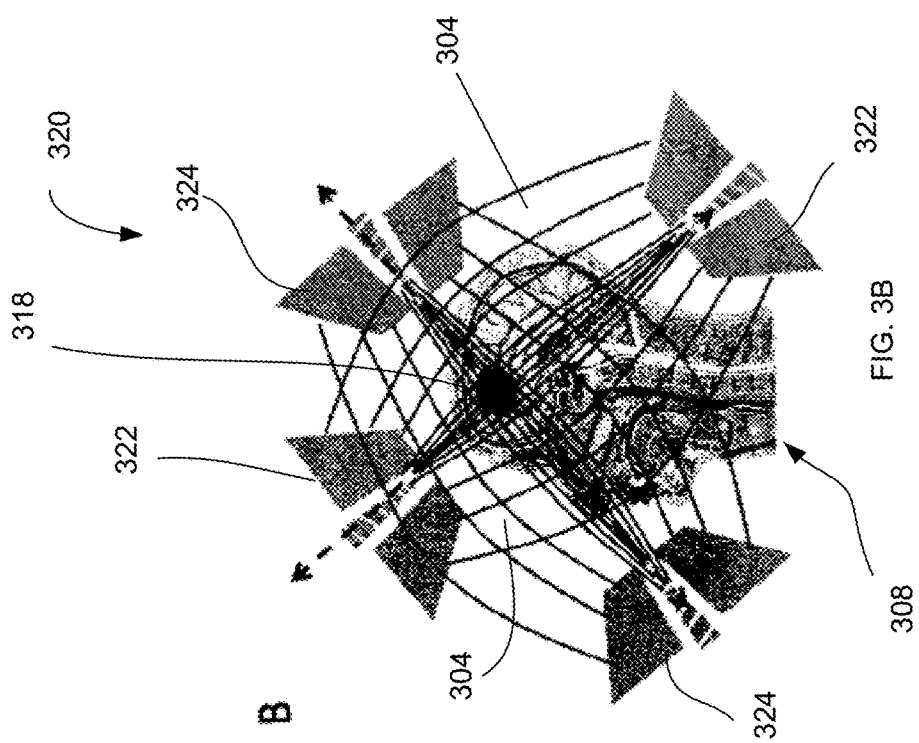
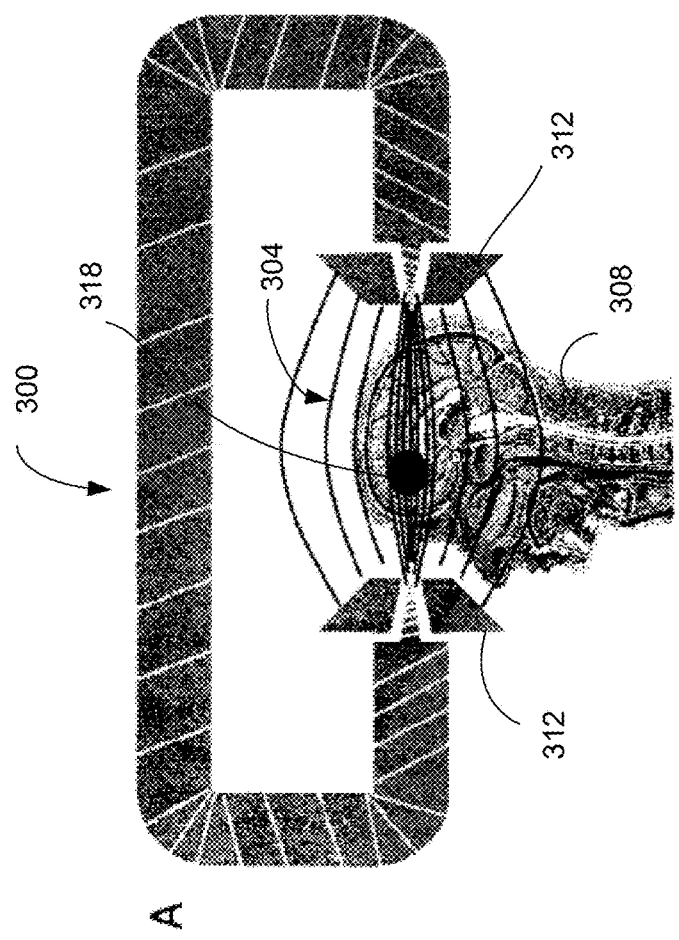
FIG. 3A
FIG. 3B

FIG. 10A
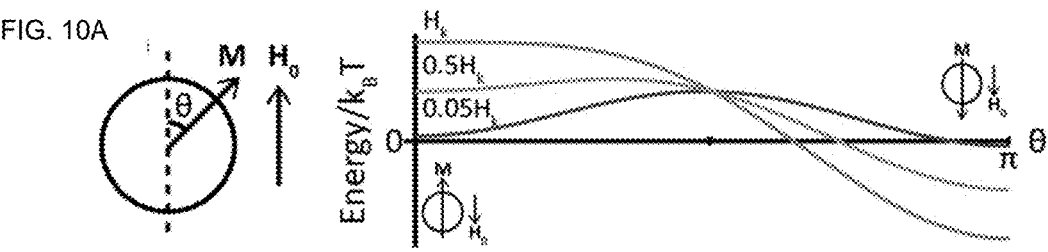
FIG. 10B
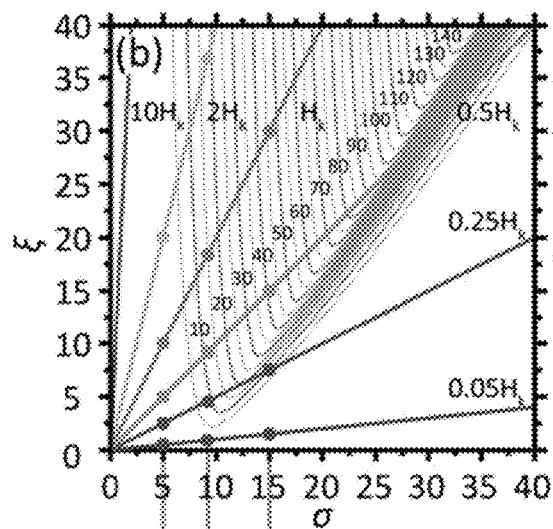
FIG. 10C
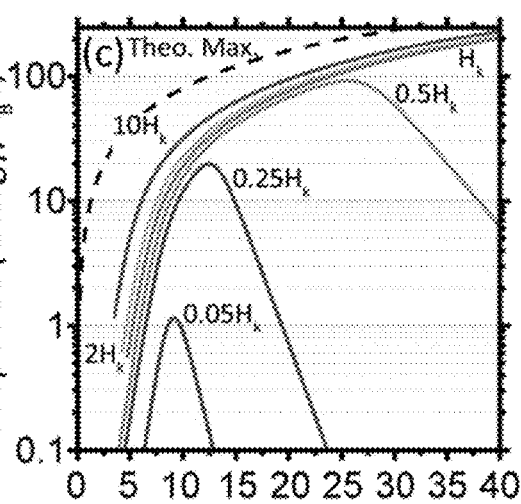
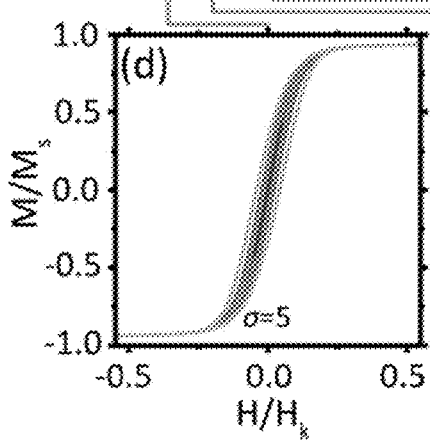
FIG. 10D
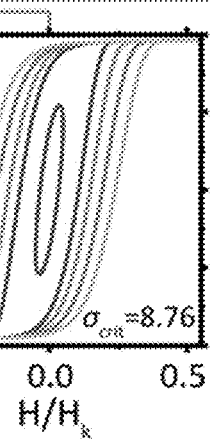
FIG. 10E
FIG. 10F

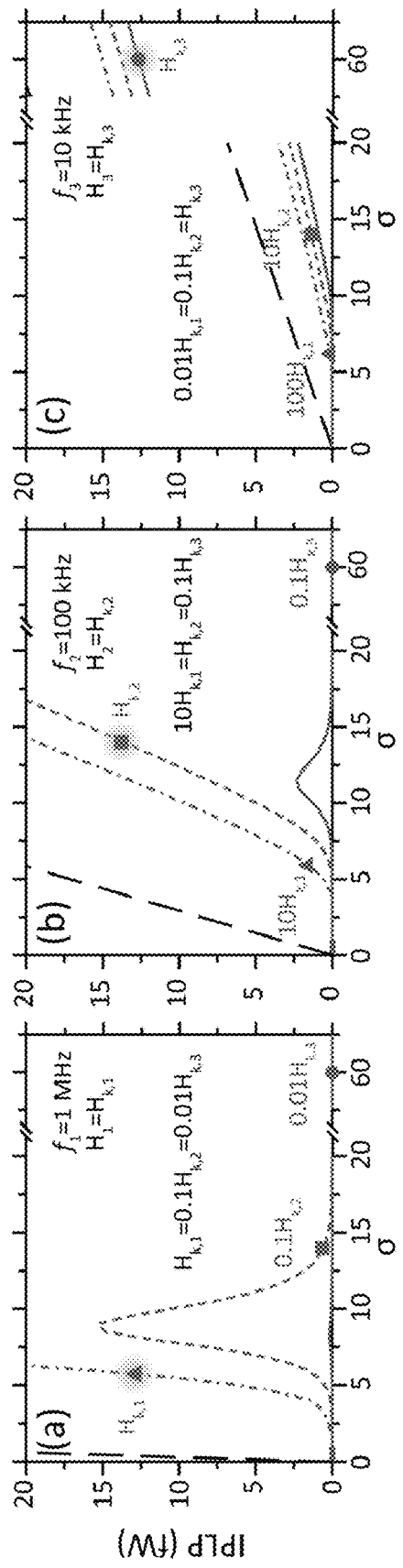
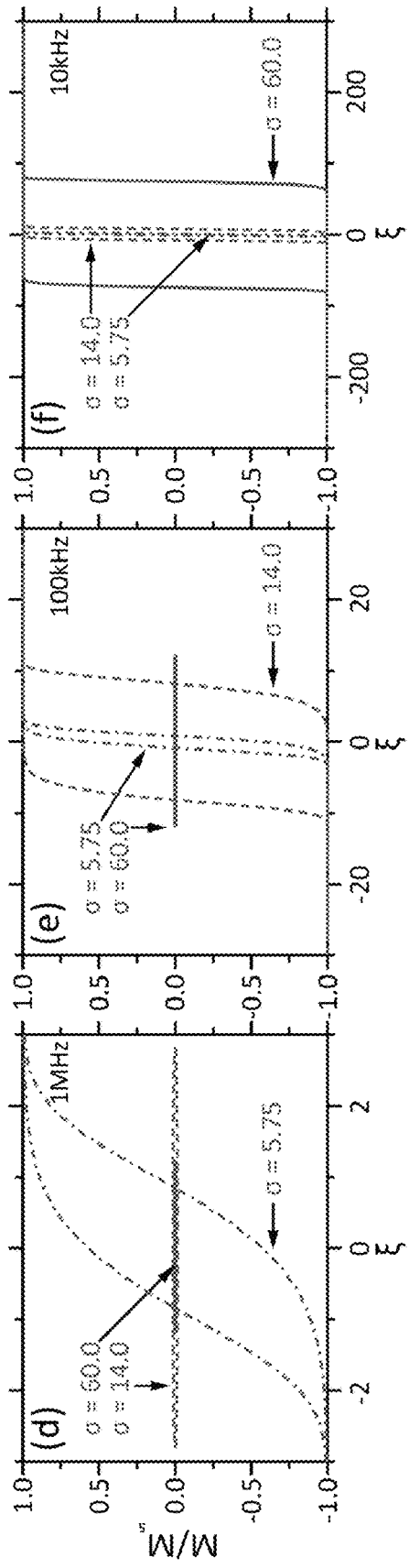
FIG. 11A FIG. 11B FIG. 11C
FIG. 11D FIG. 11E FIG. 11F

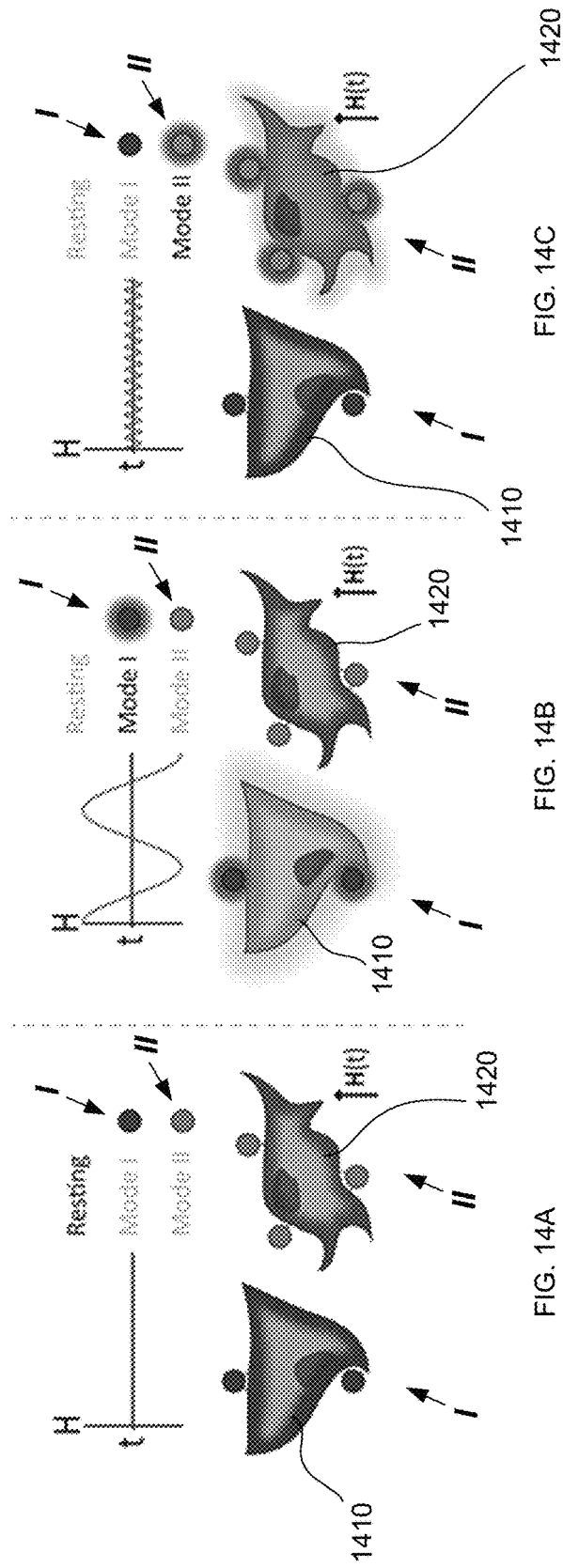

INDEPENDENT MAGNETICALLY-MULTIPLEXED HEATING OF PORTIONS OF A TARGET

CROSS-REFERENCE TO RELATED APPLICATIONS

The present application claims priority from and benefit of the U.S. Provisional Patent Application No. 61/910,395 filed on Dec. 1, 2013 and titled "Multimodal Magnetic Heating and Stimulation of Tissue". The disclosure of the above-identified patent application is incorporated herein by reference in its entirety.

TECHNICAL FIELD

The present invention relates to methods and systems configured to define targeted remote operational access to a chosen sub-volume of a bigger volume with the use of magnetic field; for example, to establish operator-guided control of temperature of the chosen sub-volume. More particularly, the present invention is directed to effectuating cellular response or function of a chosen type of cells with the help of transduction of the magnetic field into heat localized in the vicinity of the chosen cells and without operationally affecting the neighboring cells. Based on such independent magnetic-field-driven control, a cellular function switch is proposed.

SUMMARY

An embodiment of the present invention provides a method for magnetically-multiplexed stimulation (for example, heating) of a region of interest (ROI) of a volume of a target. The method includes delivering a mix of magnetic particles to the volume such as to spatially associate the first magnetic particles with a first sub-volume of the volume and the second magnetic particles with a second sub-volume of the volume, wherein the mix of magnetic particles containing first magnetic particles characterized by first parameters and second magnetic particles characterized by second parameters, at least some of the first parameters being different from at least some of the second parameters. The method further includes activating a first alternating magnetic field (AMF) and exposing an entirety of the volume to said first AMF, said first AMF having first AMF parameters defined such as to cause generation of a first loss power associated with the first magnetic particles and a second loss power associated with the second magnetic particles.

Embodiments of the invention also provide a method for magnetically-multiplexed stimulation of a region of interest (ROI) of a volume of a target containing a biological tissue. Such method includes delivering first and second magnetic particles to the ROI; and forming alternating magnetic field across the ROI, the alternating magnetic field having such alternating magnetic field parameters as to selectively heat the magnetic particles while leaving the second magnetic particles substantially unaffected by the alternating magnetic field.

Embodiments of the invention additionally provide a system structured to effectuate a multimodal stimulation of a region of interest (ROI) biological tissue and comprising a means for generating (a) spatially non-uniform magnetic field(s), throughout the ROI, characterized by at least one spatial gradient of the generated field(s) along which magnetic particles associated with the biological tissue are congregated in or about the ROI; and (b) alternating magnetic field(s) penetrating through the ROI. Optionally, the means is structured to create a constructive superposition between first and second spatially non-uniform magnetic fields and/or between first and second alternating magnetic fields.

BRIEF DESCRIPTION OF THE DRAWINGS

The invention will be more fully understood by referring to the following Detailed Description in conjunction with the generally not-to-scale Drawings, of which:

FIGS. 3A and 3B illustrate schematically examples of magnetic circuits for use with an embodiment structured to magnetically stimulate a portion of the biological tissue to which the identified magnetic particles have been delivered along a vector of a gradient of time-independent magnetic field;

FIG. 8A: The structure of one possible composite material involves superparamagnetic Fe3O4 particles embedded in a piezopolymer matrix. FIG. 8B: An alternating magnetic field is applied, producing large temperature increases in the composite particle. FIG. 8C: The enhanced polarization of the particle due to the pyroelectric property of the matrix generates an action potential by biasing the voltage gated ion channels indigenous to the neuronal membrane;

FIG. 10A shows a schematic diagram of the SDMNP in the alternating magnetic field and energy as a function of θ (angle between the magnetic moment and the easy axis of the SDMNP);

FIG. 10B includes contour plot of a hysteresis-loop area as a function of σ and ξ for uniaxial anisotropy at 500 kHz, superimposed with paths representing AMF amplitudes of different magnitude relative to $H_k$;

FIG. 10C shows a hysteresis loop area as a function of σ plotted along the paths of FIG. 10B. The dashed line represents 8σ, the theoretical maximum predicted by Stoner-Wohlfarth theory at T=OK.

FIGS. 10D, 10E, and 10F show simulated hysteresis loops for points in σ-ξ space for representative a values from the superparamgentic regime (FIG. 10D) and ferromagnetic regime (FIG. 10F), and the $\sigma_{crit}$ dividing them (FIG. 10E), which varies with frequency;

FIG. 11A illustrates simulated IPLP for SDMNPs driven by an alternating magnetic field at 1 MHz and amplitude $H_0=H_{k,1}=0.1H_{k,2}=0.01H_{k,3}$. Dash-dot-dash, dashed, and solid lines correspond to low ($H_{k,1}$), medium ($H_{k,2}$), and high ($H_{k,3}$) coercivity materials, respectively. Markers represent σ values of SDMNPs selected from each set for multiplexing. The long black dashed line represents 8σ, the theoretical maximum;

FIG. 11B provides a plot similar to that of FIG. 11A, but derived for the field of amplitude $H_0=H_{k,2}$ at 100 kHz;

FIG. 11C is a plot similar to that of FIG. 11A but derived for an alternating magnetic field of amplitude $H_0=H_{k,3}$ at 10 kHz;

FIGS. 11D, 11E, 11F show simulated hysteresis loops for the SDMNPs selected for multiplexing at the alternating magnetic fields with parameters corresponding to the plots of FIGS. 11A, 11B, and 11C, respectively. Numerical area of the $M/M_S$ vs. ξ loops is equal to individual particle loss energy per cycle normalized to ambient thermal energy. The axes are rescaled such that the graphical area is proportional to IPLP;

FIG. 13A: resting state. FIG. 13B: activation of drug release with an AMF according to mode I. FIG. 13C: activation of drug release according to mode II. Magnetic multiplexing results in multiple stage release or independent control over the release of multiple drugs;

FIGS. 14A, 14B, 14C illustrate an application of an embodiment to independently and minimally invasively provide stimulus to identified temperature-sensitive cellular structures to which the identified magnetic nanoparticles are coupled. With targeting, magnetothermal multiplexing allows for independent stimulation of different cell types, even for those located in close proximity with one another.

FIG. 15A: path-independent mechanical activation; FIG. 15B: path-dependent mechanical activation.

DETAILED DESCRIPTION

Figure 1:
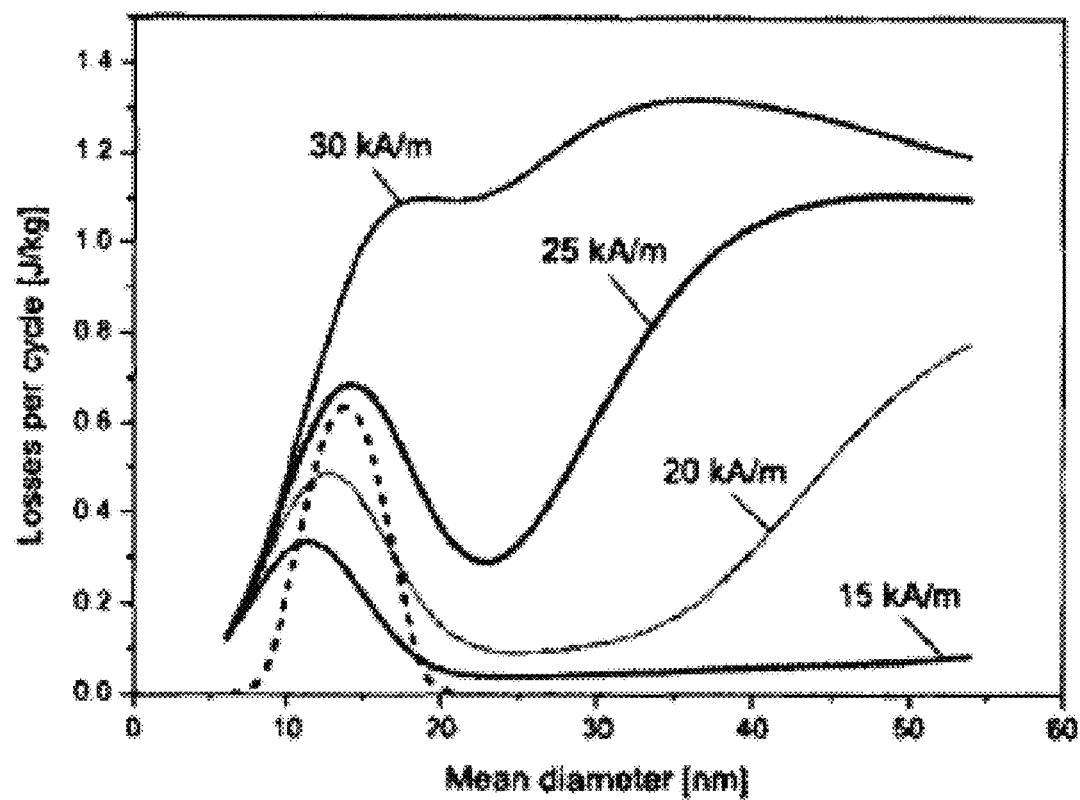
FIG. 1 is a plot representing theoretical calculations of loss (per cycle) of alternating magnetic field for magnetite. Reproduced from Hergt et al. (Nanotechnology, v. 21, p. 015706, 2010)

The present invention addresses a need for remotely and independently controlling properties of one or several chosen, optionally adjacent to each other sub-volumes of a bigger volume (a portion or portions of a whole, the stimulation of which is not depending or contingent upon the stimulation or lack thereof or operation of other portion or portions of the whole) based on the use of magnetic fields to excite different magnetic particles associated with such chosen sub-volumes. A chosen portion of the whole may be either separated from or integrated with other portions of the whole. As part of the provided solution, the specific problem of targeted, aimed access to and influencing of a selected object (such as a portion of the biological tissue, for example), is solved by associating the magnetic particles with and/or delivering such particles to the selected sub-volumes of the object (optionally—the particles suspended in a physiological solution) and exposing the particles disposed in association with the chosen sub-volumes to the magnetic field to cause a biological reaction of the chosen sub-volume of the tissue in response to the exposure.

The problem of independent access to objects or targets (selected from the multiplicity of objects or targets that have different material and/or operational properties) and selective activation of material and/or operational properties of the accessed objects or targets is solved by operationally associating, with such objects or targets, respectively corresponding magnetic particles having different particle parameters (such as, for example, sizes, shapes, anisotropy fields, magnetic hysteresis loops) and selectively exposing the chosen objects or targets to alternating magnetic fields (AMFs) and that have respectively-corresponding different strengths and/or frequencies.

The problem of multi-modal magnetic heating of identified portion of magnetic particles chosen from the multiplicity (mix) of magnetic particles (for example, at least one sub-population of magnetic particles from the overall population of magnetic particles) that have different particle properties (such as, for example, sizes, shapes, coercivities) and that are located (optionally disorderly) in proximity to one another (or even co-located in a defined macro-volume) such as to preclude the heating of the remaining portion of the multiplicity of the magnetic particles is solved by exposing the overall population of the particles to at least one alternating magnetic field, the strength and/or frequency of which are specifically chosen (i) to correspond to the parameter(s) of the at least one identified sub-population of particles and, (ii) to not both have high heat-dissipation values at the same time, or low values at the same time, or intermediate values at the same time, in contradistinction with the predictions and expectations of the linear response theory.

Various situations may require independent heating of sub-portion(s) of a whole (without affecting the remaining part(s) of the whole). Examples of such possibly not the most common-day situations include, for instance, oven-cooking of only identified produce on a plate containing several types of produce while preserving the rest of them raw or uncooked, or welding specific junctions of a complex multi-junction apparatus without affecting the remaining junctions. In the context of biological studies, such selective heating task may be required, for example, to reach and affect only nerve cells of the tissue to trigger their action potential to initiate appropriate cascades of reactions associated with such cells. Whether big or small, simplistic or complicated, the attempt to independently influence of a subpopulation, sub-part target of a larger host necessarily faces a need to effectuate such influence without operational cross-talk with those sub-parts of the host that are not of interest.

The present invention provides an approach for such remote control of a function of a specific sub-portion of a whole (and, in a specific application, for remote control of a function of a biological cell) based on the use of a magnetic field to excite magnetic particles targeted to such specific sub-portion. In the case of controlling different biological cells, the identified cells express a temperature-sensitive response while the excitation of the magnetic particles associated with (for example, being in the vicinity of) these cells causes a localized temperature increase that is transduced into the cellular response. The targeted cellular responses may include, for example, biological signaling, release of a chemical or compound, as well as destruction of the targeted cells. The idea of the invention stems in part from the realization that—when different cells of a biological tissue have corresponding affinities to different magnetic particles (or magnetic nanoparticles or MNPs, which term will be used herein interchangeably) when (due to such affinities) different MNPs are interdispersed and intermixed in the tissue to adhere and/or associate with the corresponding cells—the biological/biochemical and/or other responses of the chosen cells can be activated substantially without cross-talk with other cells of the tissue by applying magnetic field having judiciously chosen characteristics to the whole population of the MNPs in the tissue.

In the context of this disclosure, magnetically multiplexed heating of identified element(s) from the group of elements is defined as independent and selective heating of such element(s). In this disclosure, the terms "multiplexed magnetic heating", "magnetically multiplexed heating", "multi-modal magnetic heating", "magnetothermal multiplexing" and similar terms may be used interchangeably, and each of the terms refers to a process of independent (and optionally coordinated) heating of a set (or several different sets) of magnetic particles chosen from a mix of magnetic particles with different physical properties by applying magnetic field(s) the properties of which are judiciously tailored towards magnetic activation of the chosen set(s) of particles.

One implementation of the invention causes multi-modal magnetic heating (also referred to herein as magnetically multiplexed heating) of identified subpopulation(s) of (optionally, single domain) magnetic nanoparticles co-localized in the same spatial region. This is accomplished, for example, by judicious formation of material of such nanoparticles to exhibit targeted heating rates under distinct driving conditions that substantially preclude similar heating in the neighboring nanoparticle subpopulations. According to the idea of the invention, and with the use of the multi-modal magnetic heating principle as multi-modal magnetic stimulation (or magnetically-multiplexed stimulation, M3S), multiple types of (optionally, single-domain) MNPs exposed to magnetic fields characterized by multiple alternating magnetic field parameters are further employed to non-invasively (and independently from affecting the surrounding environment) actuate the identified cells and/or distinct biological processes in a tissue sample. This is achieved with the use of localized heat dissipated in such MNPs through magnetic hysteresis losses.

When a single type of magnetic particles is targeted, the activation of heat losses in such particles due to exposure of the particles to the external magnetic field is a method to remotely stimulate the activity of a cell type of interest in a subject with which the magnetic particles have been associated (for example, delivered and/or juxtaposed with and/or incorporated into). When a mix of magnetic particles of different types is used (formed, for example, from multiple materials having different geometric and/or magnetic properties), different magnetic particles can be spatially associated with different types of cells to realize switching of cell-activity activation from one type of cells to another, thereby implementing a cellular switch. For example, a mix of MNPs can include a first type of MNPs having a first magnetic hysteresis characteristic and a second type of MNPs having a second type of magnetic hysteresis characteristic such that first and second magnetic fields required to heat-up, respectively, the first and second magnetic particles differ to a degree sufficient to not cause cross-talk during the MNP-heating process. An embodiment of the invention additionally provides strategies for increasing the efficiency of M3S via alignment of the magnetic moments of the MNPs with their magnetic easy axes, for concentrating the MNPs at the specific portion of the tissue sample, and for limiting the volume of the tissue sample affected by the M3S.

The observation that magnetic particles (such as nanoparticles or at least particles of a very small size or single domain particles) experience hysteresis heating when placed in rapidly alternating magnetic fields has been addressed before. For example, in the field of high-frequency transformers this heating phenomenon, being operationally undesirable, is mitigated by engineering specific soft ferromagnetic materials. Turning this effect to practical use has also been explored. For example, some studies considered this kind of power dissipation to selectively kill tissue comprising cancerous tumors. Such studies are constantly in search of new materials with larger specific loss power (SLP) values, though effective heating strategies known to-date depend heavily on the amplitude and frequency of the employed magnetic field.

In context of the present disclosure, for applications in which selective heating of nonconductive materials in the same space requires only a reasonably mild temperature change, multimodal magnetic heating of the present invention provides a compelling strategy. MNPs are sufficiently small to be reasonably considered, by a person of ordinary skill in the art, to have single magnetic domain, and may be shaped such that their behavior in the magnetic field may be substantially dominated by material magnetic anisotropy rather than anisotropy of their shape. A mix or solution of the MNPs may be prepared to be sufficiently dilute to neglect the MNP-MNP interaction in the mix. When surrounded by a material matrix (such as a matrix of a heat-conducting host material, physiological fluid, or a biological tissue) or attached to a surface, crystal lattices of the MNPs become rotationally fixed while the orientation of the magnetic moment remains subject to the influence of the applied magnetic field. Advantages of the proposed multimodal magnetic heating (M3H) include weak interaction of alternating magnetic fields with non-magnetic, non- or weakly-conductive materials (such as plastics, non-magnetic insulating ceramics, biological matter) and a possibility for precise targeting assisted by magnetic fields. In addition, heating rates can be scaled upward by scaling up the frequency of the applied magnetic field.

Bases for Implementation of Embodiments.

In considering the heating caused by the applied magnetic field, the related art conventionally and faithfully follows a linear response theory, which is applicable in the case when the applied field is significantly lower that the zero-temperature coercive field of the material to which the magnetic field is applied. While for magnetic nano-particles that are sufficiently large to fall outside of the superparamagnetic regime, a departure from the linear response theory has been observed in a specific material, $Fe_3O_4$ or magnetite, at sufficiently high applied fields (see Hergt et al. in *Nanotech-* nology, v. 21, pp. 015706-11, 2010, the FIG. 1 of which is reproduced herein as FIG. 1), what has escaped the recognition by a person of ordinary skill in the art to-date and what the related art does not investigate in sufficient detail is a realization that—when magnetic fields of specifically-chosen parameters are employed—the deviation of the response of MNPs of various and numerous materials from the prediction of the linear response theory is subject to dynamic behavior of hysteretic properties of the materials in question. The very problem of gainfully utilizing the magnetic fields that would cause magnetic particles to react in a fashion different from that predicted by the linear response theory—let alone, the problem and solution of defining the parameters of such magnetic fields—simply has escaped the attention of skilled artisans. According to the idea of the present invention, it is the operation in the regime deviating from predictions by the linear response theory that forms the basis of the gainful multi-modal heating and independent triggering of identified sub-population of elements of a target.

Indeed, in accord with the linear response theory (LRT), in order to increase heating rates of magnetic particles, the generally accepted and used strategy of the related art (such as hyperthermia research, for example) has been to use progressively larger fields at higher frequencies. In stark contradistinction with this accepted strategy, the advantageous application of the multi-modal heating of the present invention employs magnetic fields characterized by a roughly constant field-frequency product, such that the field amplitude and frequency are varied inversely to one another over orders of magnitude. Defining the driving magnetic fields in terms of a field-frequency product according to the present invention is physically motivated by considerations of the power dissipated by eddy currents in surrounding media, the amplitude of the sweep rate of the field, and technical limitations in designing driving magnets.

The feasibility of magnetothermal multiplexing approach of the present invention relies on accounting for the effect produced by the applied alternating magnetic field (AMF) on the timescale of stochastic magnetization reversal. This effect is frequently neglected in the context of single domain (SDMNP) heat dissipation due to prevalent use of the LRT, in which the assumed "relaxation time" often has no explicit dependence on AMF amplitude. A growing body of experimental evidence indicates that the domain of validity of the LRT is more restricted than the range of conditions in which it is typically applied.

There are several approaches to develop a more generalized theory of heat dissipation in ensembles of non-interacting MNPs (for example, single-domain magnetic nanoparticles, SDMNPs) in AMFs. The idea of the present invention is rooted in the application of a more general model, the so-called dynamic hysteresis (DH), which offers an alternative treating the coherent reversal of SDMNPs' moments as kinetically limited by thermal activation over a time-varying energy barrier determined by both the SDMNP anisotropy and the Zeeman energy of its moment in the field (illustrated schematically in FIG. 10A).

The essential physics of DH is contained in the relative magnitudes of these energetic contributions normalized to the ambient thermal energy, which defines unitless parameters $\sigma$ and $\xi$ (J. Carrey, B. Mehdaoui and M. Respaud, J. of Appl. Phys. 109 (8), 083921 (2011)):

$$\sigma \equiv \frac{KV}{k_B T} \quad (1a)$$

$$\xi \equiv \frac{\mu_0 H_0 M_s V}{k_B T} \quad (1b)$$

Here, K is the effective anisotropy energy of the SDMNP, V the volume, $H_0$ the AMF amplitude, $M_S$ the saturation magnetization, and $\mu_0$ the permeability of free space. These definitions of $\sigma$ and $\xi$ assume idealized spherical single crystal SDMNPs with uniform magnetization and effective anisotropy that scales with volume regardless of contributions from surface, shape, or magnetostrictive effects. While these assumptions do not fully describe the complexity of real SDMNPs, identifying the physical origins of a is not conceptually essential for the multiplexing approach according to the idea of the present invention. While the DH-based theoretical model underlying the present disclosure follows the work of Carrey et al., several notable mathematical and interpretational differences are employed to form a modified DH approach. In particular:

1) Easy alignment of the SDMNPs is assumed so that the results that can be interpreted as a predicted upper bound.

2) Thermal spreading of the moments about the easy axes is estimated by a Boltzmann distribution for a second order Taylor expansion of the local energy minima, labeled A and B. The magnetization M normalized to $M_S$ is given by $$\frac{M}{M_s} = C_A P_A + C_B P_B, \quad (2)$$

where $P_A$ and $P_B$ are the probabilities of SDMNP moments occupying the minima at $\theta=0$ and $\theta=\pi$, respectively. $C_A$ and $C_B$ are terms that account for the projection of these moments along the easy axis while taking into account thermal spreading:

$$C_A = \frac{\int_0^{\frac{\pi}{2}} \sin\theta\cos\theta\exp\left[\frac{-(\xi+2\sigma)}{2}\theta^2 + \xi\right]d\theta}{\int_0^{\frac{\pi}{2}} \sin\theta\exp\left[\frac{-(\xi+2\sigma)}{2}\theta^2 + \xi\right]d\theta} \quad (3)$$

$$C_B = \frac{\int_{\frac{\pi}{2}}^{\pi} \sin\theta\cos\theta\exp\left[\frac{(\xi-2\sigma)}{2}(\theta-\pi)^2 - \xi\right]d\theta}{\int_{\frac{\pi}{2}}^{\pi} \sin\theta\exp\left[\frac{(\xi-2\sigma)}{2}(\theta-\pi)^2 - \xi\right]d\theta} \quad (4)$$

This affects calculated power dissipation rates by less than a few percent for most $\sigma$ and $\xi$ combinations, but avoids the hyperbolic tangent-like saturation for superparamagnetic SDMNPs that is predicted by constraining the moments to the easy axes.

3) For applications that rely on local heating, individual particle loss power (IPLP) is a more relevant metric than the SLP of an ensemble. For the purposes of this disclosure and the appended claims, the SLP is defined as the power dissipated per gram of metal content of the MNPs (for instance measurable in units of watts per gram). It is an intensive quantity that is most useful in applications where collective (bulk) heating is required. In comparison, the IPLP is defined as the population-averaged power dissipated by a single MNP, for instance considered in units of femtowatts. It is an extensive quantity that is relevant to situations where heating effects of individual nanoparticles are most relevant, such as chemical payload release.

To calculate IPLPs, we consider $M/M_S$ vs. $\xi$ hysteresis loops, with an area equal to the individual particle loss energy per cycle of the AMF normalized to the ambient thermal energy. The results can be extended to SLPs by making assumptions about SDMNP volume V and mass density $\rho$. The maximal area of these hysteresis loops is predicted by Stoner-Wohlfarth theory and is equal to $8\sigma$.

The area of these $M/M_S$ vs. $\xi$ hysteresis loops, proportional to IPLPs, can be plotted in a $\sigma$-$\xi$ space at a given AMF frequency (FIG. 10B). Defining the anisotropy field $H_k$ as the applied field at which the barrier to reversal vanishes, the ratio $\xi/(2\sigma)$ can be rewritten as $H_0/H_k$, describing a linear path through the origin of $\sigma$-$\xi$ space with a slope determined by the magnitude of the AMF amplitude (FIGS. 10B, 10C). In the limit of low AMF amplitudes (i.e., $H_0 \ll H_k$), a critical $\sigma_{crit}$ value occurs where the mean lifetime of stochastic magnetization reversal in the absence of an AMF is equal to the timescale of measurement set by its frequency. For low AMF amplitudes, $\sigma_{crit}$ corresponds to the maximum SLP predicted by LRT. Moments on either side of this maximum either escape more rapidly or more slowly than the timescale set by the AMF frequency, which divides the superparamagnetic and ferromagnetic regimes, respectively. The simulations made according to the modified DH approach predict markedly different dependence of IPLP on AMF amplitude for the two regimes. (See FIGS. 10D, 10E, 10F for plots of the hysteresis loops.)

With this graphical representation, the strategy for efficiently producing maximal IPLPs with the constraint of a given $H_0 f$ product seems clear (FIG. 10C). Large SDMNPs driven by AMFs with $H_0$ approaching or exceeding $H_k$ at high frequencies produce hysteresis loops approaching the theoretical limit set by the material, provided that the fastest available relaxation process is coherent reversal and the detailed dynamical picture of damped precession can be neglected. This strategy was borne out experimentally in the highest heating rates reported, where a high $H_0 f$ product is used and "tuning" of materials parameters has little to do with attaining $\sigma_{crit}$ and instead involves finding the largest SDMNPs in which coherent reversal still dominates. Therapeutic limitations on the allowable $H_0 f$ product make it more pragmatic to reframe the problem of optimization as one of adjusting material parameters to make best use of a set of available driving conditions. This suggests the possibility of multiplexed heating by selecting materials with properties that lead to dramatically different optimal driving conditions with a similar $H_0 f$ product.

In order to render the multi-modal heating (magnetically multiplexed heating) methods of the present invention practical and operationally useful, the employed MNPs may be chosen to exhibit low heating efficiency under most driving conditions, and, at the same time, preferably a higher heating efficiency for one specific set of the driving conditions that corresponds to the targeted MNPs. In one implementation, this is accomplished by deploying MNPs the size of which is larger than the optimal size of the magnetic particles predicted by linear response theory and initially driving such particles with fields having amplitudes nearing or exceeding their zero-temperature coercive field. By increasing the frequency and simultaneously lowering the field amplitude (in contradistinction with the methods employed in related art), the heating-per-cycle in the NPs with the highest anisotropy should drop significantly enough to offset the gain from more rapid cycling. The power parameter describing the dependence of heating in larger particles as a function of field is higher than that of the LRT. When utilizing lower fields, the heating of such larger particles is more effective than the LRT would predict. Meanwhile the effective hysteresis loops of NPs with lesser anisotropy density are less affected if the lower-strength magnetic field still approaches their zero-temperature critical anisotropy field.

Feasibility.

Figure 2C:
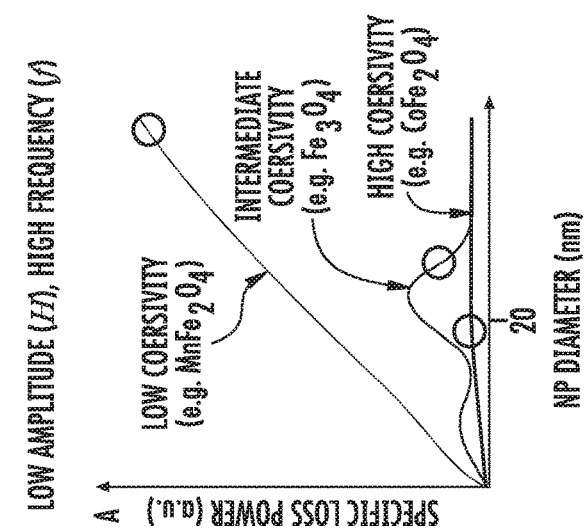
FIGS. 2A, 2B, 2C are plots of expected specific loss power (SLP) s a function of particle size, shown for three different materials (that have different anisotropy properties) and three sets of alternating magnetic field parameters.
Figure 2B:
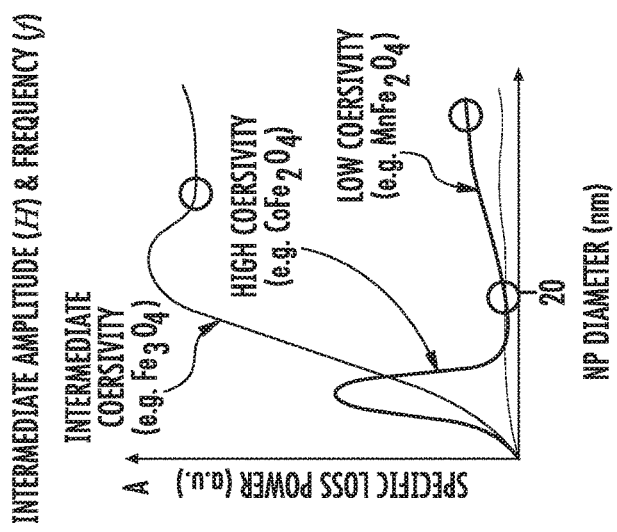
Figure 2A:
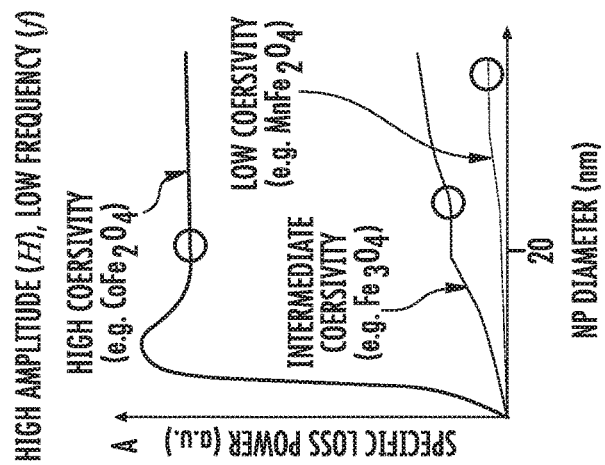

FIGS. 2A, 2B, and 2C provide plots illustrating the principles associated with of the present invention. Here, expected specific loss power (SLP) as a function of particle size is shown schematically for three materials with different coercivities (anisotropy energy density constants, K) and three sets of alternating magnetic field (AMF) parameters. In each of FIGS. 2A, 2B, and 2C, one curve corresponds to a high coercivity material (such as $CoFe_2O_4$, K~$4.5*10^5$ J/m$^3$ or an engineered composite with a somewhat lower effective K), another curve corresponds to an intermediate coercivity material (such as $Fe_3O_4$, K~$1.4*104$ J/m), and a third curve corresponds to a low coercivity material (such as, for example, $MnFe_2O_4$, K~$1.5*103$ J/m$^3$). FIG. 2A corresponds to high-amplitude and low-frequency AMF, e.g. f~2.5 kHz and $H_o$~1400 kA/m. FIG. 2B represents intermediate-amplitude and intermediate-frequency AMF, e.g. f~100 kHz and $H_o$~30 kA/m. FIG. 2C illustrates the dependencies for a low-amplitude and high-frequency AMF, e.g. f>1 MHz and Ho=0.5 . . . 2 kA/m. It is appreciated, that the SLP values may also depend not only on the size of a magnetic particle made from a chosen material, but also on the particle geometry.

The operational regime of a magnetic-particle-heating may be chosen such that a field-frequency product remains substantially constant. Such optional choice is based on realization that, at very low applied field, a dependency of a specific loss power (SLP) on the size of a NP will have a peak at a value of anisotropy energy where the rate of stochastic escape over the barrier matches the driving frequency. For anisotropy energies below that value (that is, in the superparamagnetic regime of Carrey et al. in J. of Appl. Phys, v. 109, p. 083921), the escape over the barrier occurs too rapidly during the cycle for optimal population reversal. For anisotropy energies above that value (in the single domain ferromagnetic regime), too few magnetic moments escape over the barrier to align with the field for optimal population reversal. As the strength of the field is increased, the situation is not significantly improved for the NPs in the superparamagnetic regime. Above the critical value of applied magnetic field, however, embodiments of the present invention draw on sufficient improvement for the larger-size NPs because the energetic barrier to population inversion now completely vanishes for part of the cycle. Such behavior is not predicted by linear response theory and has not been addressed in related art for a variety of magnetic materials.

According to the above-outlined principles, the use of MNPs can be advantageously employed to actuate non-invasively and independently distinct biological processes and/or cell types by means of localized heat dissipated through magnetic hysteresis losses. Magnetically-driven signaling (the general idea of which is to apply a rapidly alternating magnetic field to MNPs that are concentrated near cellular structures of interest, potentially via biochemical targeting) can be used for interfacing biological and electronic systems, for example. The heating of the MNPs in the applied magnetic field is directed not to heat the surrounding cells sufficiently to kill or injure them, but rather to use such magnetic-field-caused targeted heating as a stimulus to produce a desired response from the specific cells to which the chosen MNPs have affinity. In this case, proteins (such as, for example, those of a transient receptor potential, TRP, family) that undergo conformational changes relevant to their function within a few degrees of body temperature can be targeted directly and stimulated by the heating of the MNPs alone (see, for example, Huang, H. et al., *Nature Nanotechnology*, S:602-606, 2010). As a possible alternative, an indirect mechanism of influence such as the release of relevant signaling chemicals or drugs from the targeted MNPs in response to heating can be employed (see, for example, von Maltzan et al., 2007).

In a specific case, and in further reference to FIGS. 2A, 2B, 2C, the magnetically multiplexed heating approach to addressing specified cells of a biological tissue utilizes the affinities that MNPs of stable magnetic oxides $MeFe_2O_4$ (where Me=Ni, Mn, Co, Fe, Zn, for example), that are characterized by different anisotropy fields, exhibit to various biological cells. Such MNPs are utilized to interact with alternating magnetic fields of different amplitudes and frequencies to locally heat the targeted cells and to trigger different cell reactions associated with the targeted cells. Magnetic field-to-heat energy conversion (expressed through specific loss power) is optimized via alignment of MNP magnetic moments along the magnetic easy axis. A strong uniform, non-time varying magnetic field would preferentially align the easy axes of particles with the field in a weakly viscous medium. Uniform fields align moments of particles with the field direction without exerting a net force. Assuming that the moment is aligned with the field over long timescales, the torque tending to physically orient the particle will favor the easy axis with the magnitude of that torque being proportional to the anisotropy of the particle. This process of aligning particles can be gainfully applied to situations where through e.g. chemical attachment or solidification of a surrounding matrix, subsequent rotation is prevented.

Methods of delivery of the mix of MNPs to identified locales of the target for the following magnetically multiplexed heating of such locales can differ in different embodiments. For example, optionally, in one implementation the three-dimensional (3D) positioning and/or spatial localization of the MNP(s) to a defined volume of the body that is different from the site of initial injection or placement of the MNPs in the biological tissue is effectuated with the use of gradients of time-constant (DC) magnetic fields (as well as 3D-focusing of the alternating magnetic fields). As MNPs possess large magnetic moments, the MNPs move in the tissue driven by gradient(s) of magnetic field throughout the target biological tissue.

Generation of magnetic fields with spatial gradients facilitating spatial concentration of MNPs at a targeted point influences the geometry of magnetic coil(s) used in a system of the present invention. In reference to FIGS. 3A and 3B, for example, such magnetic field gradients 304 throughout the tissue 308 can be formed with a combination of a few (X, Y, Z) magnetic-core solenoids (coils) 312 of split-toroidal shape. Here, FIG. 3A illustrates schematically a magnetic circuit 300 having a pair of coils 312 separated by a gap containing the tissue 308. The coils 312 are spatially tapered towards the targeted tissue 308 and that have increasing density of windings serving to more strongly magnetize the ferrite ceramic material shown as 318 and juxtaposed with (within) the tissue 308. The wide outer piece at each tip shown in cross section provides a high permeability path back into the magnetic circuit for fringed fields. FIG. 3B illustrates, in a cross-sectional view, an implementation 320 utilizing constructive superposition between magnetic fields formed by orthogonally disposed pairs of coils 322, 324 according to an embodiment of the present invention. A third coil pair, oriented perpendicularly (along an axis perpendicular to the plane of FIG. 3B) is not shown and maybe optionally used to additionally spatially tune magnetic fields' gradients to properly localize the particles (material 318). The spatial focusing of the MNPs can be further improved by surface functionalization and biochemical targeting, resulting in selective affixation of the MNPs to targeted cells once the spatial focusing and/or localization has been accomplished.

In a specific embodiment, the same pair of coils can be used to apply both the DC and AC magnetic fields to the targeted tissue containing MNPs, particularly if the geometry of the coil(s) maximizes the strength of the field at the site of stimulation. In a DC mode, the solenoid core can be saturated to generate high-level magnetic fields and contribute to the concentration of the MNPs at the site of stimulation, while a high-frequency AC mode can be additionally sequentially activated to stimulate different biological processes through multimodal magnetic stimulation.

Figure 4:
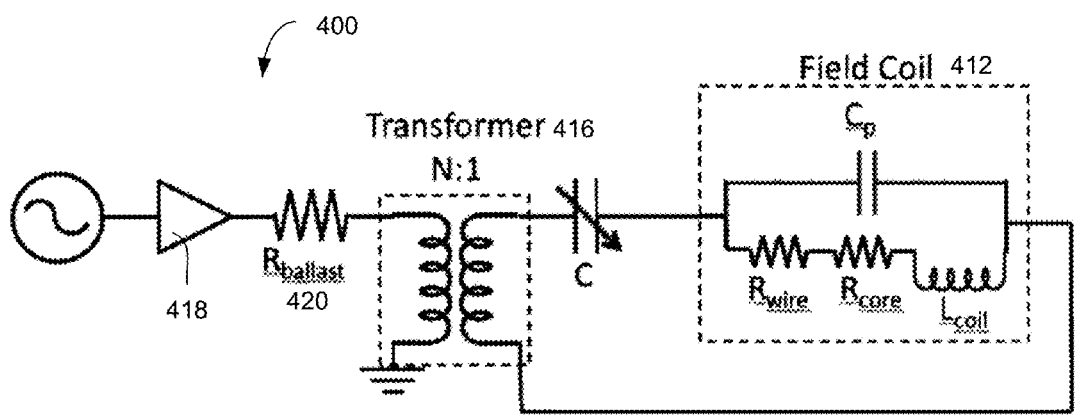
FIG. 4 depicts a schematic of the circuit structured to drive a coil with a soft ferromagnetic core and behaving as a non-ideal inductor with an associated parasitic capacitance $C_p$ and resistive losses in the wire and magnetic losses in the core.

According to the idea of the present invention, the M3S is facilitated with the use of magnetic fields having large amplitudes at low frequencies and/or magnetic fields having small amplitudes at high frequencies, which suggests that employment of a soft ferromagnetic material for a coil 312 may be preferred in some embodiments. If the time to achieving the steady-state operation is substantially shorter that the intended timescale of magnetic stimulation of the tissue, a serial LRC circuit (the example 400 of which is shown in FIG. 4) can be used in combination with amplifier(s) characterized by substantially lower input power(s) (at least in comparison with power levels experimentally used at this time in hypothermia-related art) can be used to drive such a field-coil 412. The coil may operate as a non-ideal inductor with an associated parasitic capacitance $C_p$ and resistive losses in the wire and magnetic losses in the core. The MNPs to be targeted by the magnetic field could be used in concentrations sufficiently low to ensure that the actual power dissipation in the circuit be negligible compared to the core. The transformer 416 allows the output impedance of the amplifier 418 to be more closely matched, while still generating the necessary high currents. The ballast resistor 420 stabilizes operation of the circuit 400 to variations in effective resistance introduced by the core and wire of the coil 412. Optionally, a change in amplitude and/or frequency of the signal providing input to the amplifier 418 can be established according to the desired sequence of stimulation and, optionally, with the use of a programmable electronic circuitry.

Maximizing Hysteretic Losses in Magnetic Ferrite NPs for Use as Heat-Dissipation Agents.

The discussion below addresses a problem of optimizing heat-dissipation characteristics of MNPs in alternating magnetic fields on the example of magnetic ferrite $MeFe_2O_4$ (Me=Mn, Fe, Co, for example) nanoparticles and presents experimentally observed some of the highest SLP values reported to date at a given AMF amplitude and frequency, which SLP values are in qualitative agreement with a generalized physical model of hysteretic power dissipation that can be used for the simulation-driven design of MNPs tailored for a specific biomedical application.

The ability to tune the material properties of ferrite magnetic nanoparticles $MFe_2O_4$ supports a variety of biomedical applications. For example, achieving a high magnetic moment is essential, for example, for magnetic resonance imaging (MRI) contrast agents, while maximizing power dissipation in AMFs is desirable for heat-induced necrosis of tumor tissues. Control over the size, shape, composition, and/or surface passivation of superparamagnetic MNPs is gainfully employed in magnetic hyperthermia clinical method, while AMF-induced heat dissipation in MNPs has also found new applications in remote control of cellular signaling and gene transcription in vivo. For therapeutic purposes, the administration of the MNPs into a biological tissue is subject to low concentrations of MNPs and the product of AMF's frequency f and amplitude $H_o$ should be less than $5 \times 10^9$ $A \cdot m^{-1} \cdot s^{-1}$, a figure of merit intended to limit non-specific heating of healthy tissue via eddy currents induced by the applied AMF. As a result, the field parameters are usually limited to amplitudes 5-20 $kA \cdot m^{-1}$ and frequencies below 1 MHz. In order to achieve the desired therapeutic effect under the field frequency product constraint, the MNP power dissipation rate (per gram of MNP material), or specific loss power (SLP), has to be optimized. According to a method of the present invention, such optimization, not addressed to-date by related art, was carried out based at least in part on the determination of the magnetic hysteresis losses of the MNPs in relation to their saturation magnetization, $M_S$, and the effective anisotropy energy barrier parameters as functions of amplitude and frequency of the AMF.

An ensemble of MNPs dissipates heat when magnetic moments of individual MNPs overcome anisotropy energy barrier to realign with an applied field to reduce their configurational energy. The transition of moments over the barrier is thermally activated, so that the expected power dissipation depends not only on the amplitude of the applied field's perturbation to the anisotropy energy landscape, but also the ambient temperature and cyclic timescale of the perturbation.

Accordingly, the relative magnitude of the applied field can be considered in relation to the zero temperature anisotropy field (which is defined as a field magnitude at which the barrier to coherent reversal vanishes for uniaxial MNPs). Based on such consideration, the hysteretic power dissipation of MNPs can be divided into several regimes: a) the applied field strength is below the anisotropy field; b) the applied field is above the coercive field; and c) the intermediate regime.

At field amplitudes well below the anisotropy field, the barrier is not significantly perturbed and the magnetization of the MNP ensemble scales substantially linearly with the applied field. In this regime, hysteretic losses can be appropriately modeled with the LRT (see for example, Rosensweig, *J. Magn. Magn. Mater.*, v. 252, pp. 370-374, 2002). It is recognized, therefore, that in this regime the increase of the viscosity of the host material surrounding MNPs does not necessarily dramatically alter the SLPs, and, therefore, the magnetization reversal can lead to significant heating. Field amplitudes commonly used for therapeutic purposes may significantly perturb the anisotropy barrier, particularly for materials with low anisotropy values (i.e., $MnFe_2O_4$, $K_1 = 3.0 \times 10^3$ J $m^{-3}$ or $Fe_3O_4$, $K_1 = -1.4 \times 10^4$ J $m^{-3}$). At sufficiently high applied fields, a chosen magnetic material approaches saturation. As a result, SLP values of the MNPs exposed to such fields simply cannot be made arbitrarily large by increasing the field amplitude and frequency, which finding is in stark contradistinction with the prediction of the functional form of the conventional LRT. Thus at therapeutically relevant field amplitudes, the use of LRT is limited to materials with comparatively high anisotropy energy, such as $CoFe_2O_4$ ($K_1 = 2.0 \times 10^5$ J $m^{-3}$), or, additionally or alternatively, low amplitude magnetic field. Assuming that MNPs with coercive fields much higher than the applied field are able to rotate freely, the majority of the hysteretic loss is attributable in this case to frictional heat generated by the rotation of the particle in the medium.

In the limit of field amplitudes larger than the anisotropy field, the shape and area of the resulting hysteresis loops approaches, but does not exceed the theoretical limit for uniaxial single-domain MNPs described by the Stoner-Wohlfarth model at 0 K (Stoner, E. C. et al., in *Philosophical Transactions of the Royal Society of London. Series A. Mathematical and Physical Sciences*, pp. 599-642, 1948).

In the intermediate regime, when the AMF amplitude is less than the coercive field but still perturbs the barrier significantly, the assessment of the SLP values required numerical modeling. To establish the dependence of the SLP and hysteresis loops of a ferrite material on the dimensions of the particles, the modified numerical algorithm based on the model of Carrey et al., *J. Appl. Phys.*, v. 109, 083921-083917, 2011 was used, as discussed below.

Comparison of Empirical Results with Results of Calculations.

Modeling with the Use of a Modified DH Approach.

FIGS. 11A, 11B, 11C, 11D, 11E, and 11F provide the results of verification of the above-identified principles (discussed in reference to FIGS. 2A, 2B, 2C) via modeling of the magneto-thermal multiplexing with the modified DH-approach, and guidelines of choosing the combinations of MNPs and respectively-corresponding AMFs for selective heating of a given subset of the chosen MNPs. These Figures provide an example of magnetothermal multiplexing employing three materials with $H_k$ values differing by orders of magnitude: $100H_{k,1} = 10H_{k,2} = H_{k,3}$. Here $H_{k,1}$, $H_{k,2}$, and $H_{k,3}$ are the anisotropy fields of idealized low, medium, and high coercivity materials, respectively. FIGS. 11A, 11B, 11C display IPLPs of these materials at three AMF amplitude and frequency conditions selected to maintain a constant $H_0 f$ product. From the IPLP vs σ plots, particular σ values can be chosen that dissipate significant power at only one of the three driving conditions. The hysteresis loops corresponding to these selected σ values are shown in FIGS. 11D, 11E, 11F.

As indicated by FIGS. 11A through 11F, one strategy for multiplexing with IPLPs is to use SDMNPs with differing $H_k$, however multiplexing with SLPs can be accomplished using SDMNPs with the same $H_k$ and different σ values. It is notable that multiplexing with either IPLPs or SLPs relies upon the same dependences of heat dissipation on AMF amplitude and frequency. The proof of concept for SLP multiplexing in a single material system was empirically procured with the use of $Fe_3O_4$ SDMNPs of different diameters and utilizing (i) a low-frequency-high-amplitude (e.g., 100 kHz, 35 kA/m) AMF mode of particle heating and (ii) a high-frequency-low-amplitude AMF mode (e.g., 2.5 MHz, 5 kA/m) of particle heating.

Based on the presented numerical assessments, a person of skill in the art will appreciate that MNPs made of different materials and/or of different sizes are required to activate heat dissipation when an AFM having a pre-determined amplitude-frequency combination is used, such as to maximize the corresponding SLP and hysteretic losses.

Chemical Synthesis of Magnetic Particles.

Figure 5:
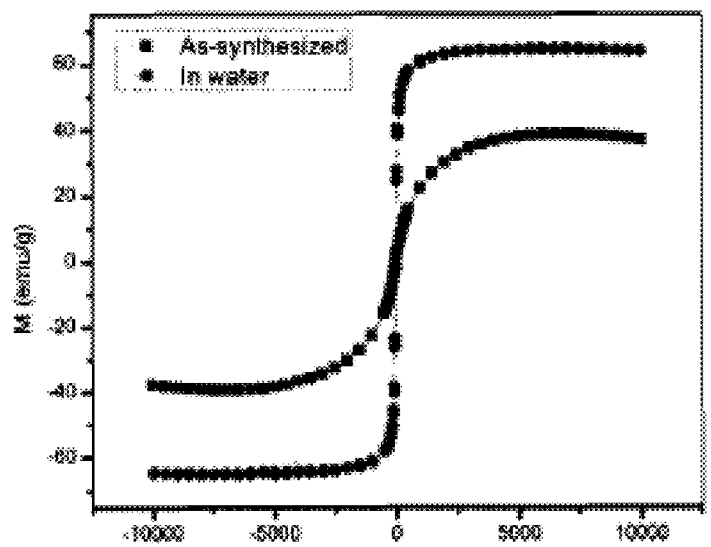
FIG. 5 shows plots representing an example of room-temperature vibrating sample magnetometer measurement of 18 nm $Fe_3O_4$ particles before and after ligand exchange form hydrophobic to aqueous media.
Figure 6A:
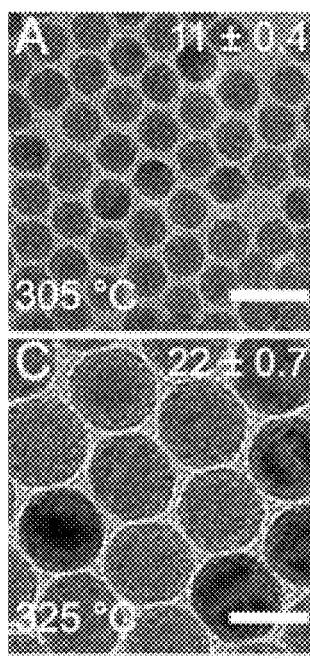
FIGS. 6A, 6B, 6C, 6D, 6E, 6F, 6G, 6H, 6I, and 6J presents transmission electron microscopy images of MNPs that have been synthesized via the thermal decomposition of metal-oleate precursors for use with an embodiment of the invention.
Figure 6B:
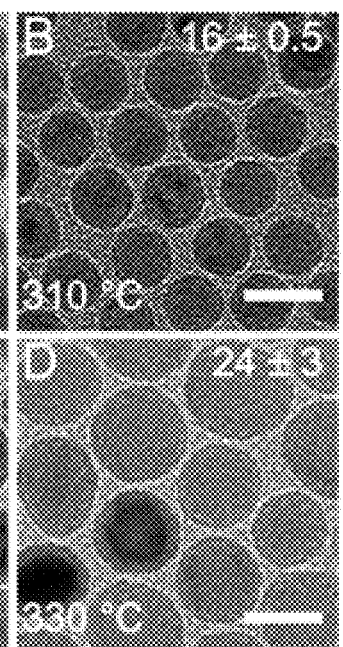
Figure 6C:
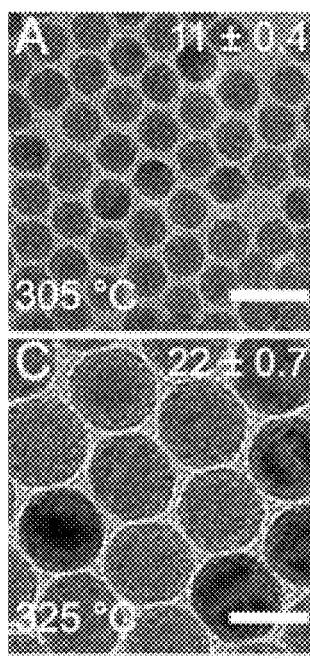
Figure 6D:
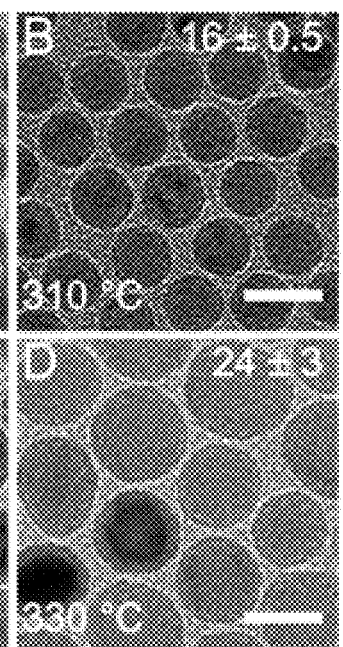
Figure 6E:
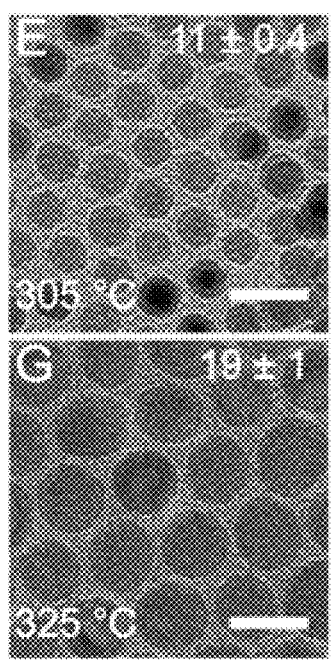
Figure 6F:
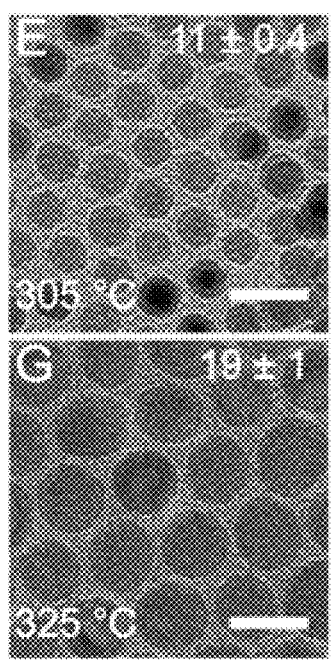
Figure 6G:
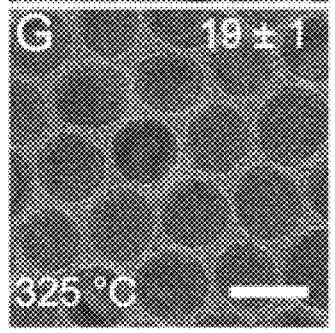
Figure 6H:
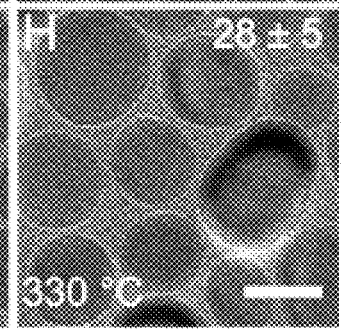
Figure 6I:
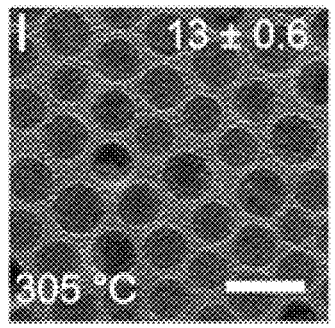
Figure 6J:
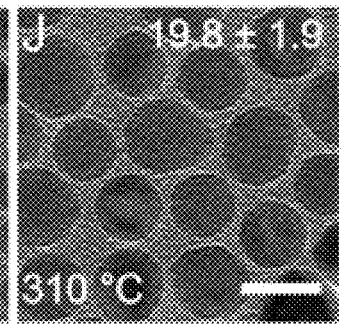

To achieve non-overlapping channels of transduction of the magnetic field into localized heating, the naturally occurring differences in anisotropy energy of magnetic particles are desirable and useful. It was discovered that thermal decomposition of metallo-organic precursors dissolved in high boiling point organic solvents in the presence of coordinating ligands is one of the best methods to prepare monodisperse and uniform MNPs with tunable composition and size. We have found that the magnetic properties of the as-synthesized NPs can be drastically improved by phase transfer into water using a high-temperature ligand exchange approach, with an unexpected result of nearly doubling the saturation magnetization from 35 emug to 65 emu/g, as shown in FIG. 5.

A set of ferrite nanoparticles with magnetic anisotropy energy constants varying over three orders of magnitude (including ferrite particles with diameters in the range from about 6 nm to about 30 nm) have been synthesized and optimized FIG. 6 presents transmission electron microscopy images of MNPs synthesized via the thermal decomposition of metal-oleate precursors with diameter, the standard deviation (nm), and the synthesis temperature values indicated on the images. FIGS. 6A 6B, 6C and 6D show iron oxide MNPs synthesized at 305, 310, 325° C. in octadecene yielding 11 nm, 16 nm, and 22 nm diameter MNPs respectively. The 24 nm MNPs were synthesized at 330° C. in eicosane. FIGS. 6E, 6F, 6G, and 6H illustrate manganese ferrite MNPs synthesized at 305, 315, 325° C. in octadecene yielding 11 nm, 16 nm, and 28 nm diameter MNPs respectively. The 28 nm MNPs were synthesized at 330° C. in eicosane. FIGS. 6I and 6J show images of 13 nm and 20 cobalt ferrite MNPs synthesized at 305° C. For 20 nm particles, the heating rate was increased to 3.3° C./min to 310° C. Scale bar length corresponds to 20 nm in each of the images.

Figure 7A:
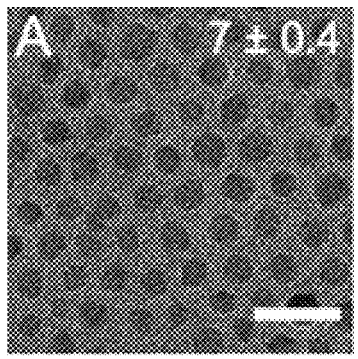
FIGS. 7A, 7B, 7C, 7D, 7E, and 7F present TEM images of $MFe_2O_4$ MNPs that have been synthesized from the thermal decomposition of metal acetylacetonate (acac) precursors.
Figure 7B:
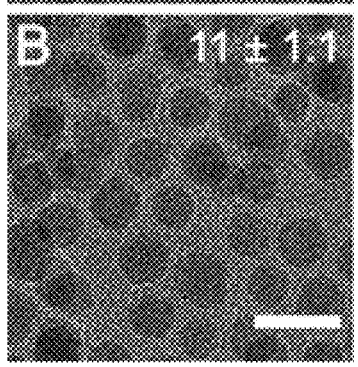
Figure 7C:
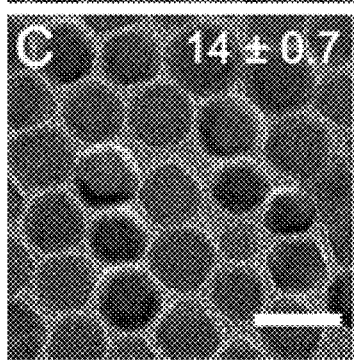
Figure 7D:
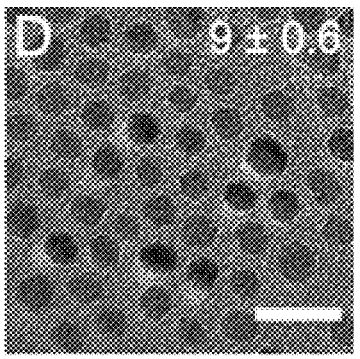
Figure 7E:
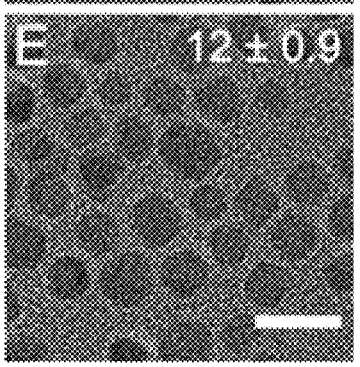
Figure 7F:
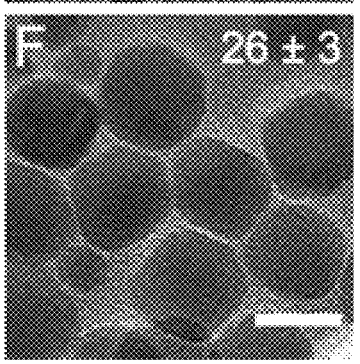

FIGS. 7A, 7B, 7C, 7D, 7E, and 7F present TEM images of $MFe_2O_4$ MNPs synthesized from the thermal decomposition of metal acetylacetonate (acac) precursors. The size and the corresponding standard deviation (in nm) are indicated on the images. Here, FIGS. 7A, 7B, and 7C show cobalt ferrite MNPs with diameters of 9, 12, and 14 nm; FIGS. 7D, 7E, 7F show manganese ferrite MNPs with diameters 7, 11, and 26 nm. The length of the scale bar is 20 nm for each image.

Magnetic properties of as-sythesized and water soluble magnetic particles of FIGS. 6A through 6J and FIGS. 7A through 7F at 300 K are further summarized in Table 1, in which the average diameters d were obtained from the TEM images of FIGS. 6 and 7, and magnetic diameters ($d_{mag}$) were obtained from linear fits of root temperature hysteresis curves in the low field range. Data marked with an asterisk (*) indicate that a particular sample was measured from water-soluble MNP solutions. The $\Phi_{Ferrimagnetic}$ indicates the volume fraction that is ferromagnetic. The bracketed values indicate the volume fraction after phase transfer into water.

TABLE 1

| Sample | d (nm) | $d_{mag}$ (nm) | $d_{mag}$* (nm) | $M_s$ (300 K) (emu/g) | $M_s$* (300 K) (emu/g) | $\Phi_{Ferri-magnetic}$ |
|---|---|---|---|---|---|---|
| Iron | 11 | 9.2 | 9.1 | 28 | 70 | 0.58 (0.56) |
| Oxide | 16 | 8.5 | 13.1 | 18 | 69 | 0.15 (0.55) |
| Oleate | 18 | 9.6 | 16.6 | 39 | 64 | 0.15 (0.78) |
|  | 22 | 9.8 | 18.8 | 41 | 65 | 0.09 (0.62) |
|  | 24 | 10.5 | 16.3 | 22 | 67 | 0.08 (0.31) |
| $MnFe_2O_4$ | 11 | 7.7 | 7.6 | 8 | 47 | 0.34 (0.33) |
| Oleate | 16 | 10.8 | 10.2 | 13 | 54 | 0.31 (0.26) |
|  | 19 | 9.8 | 9.6 | 5 | 25 | 0.14 (0.13) |
|  | 28 | 9.0 | 11.4 | 3 | 31 | 0.03 (0.07) |
| $CoFe_2O_4$ | 13 |  |  | 15.2 | 30.8 |  |
| Oleate | 20 |  |  | 3 | 7 |  |
| $MnFe_2O_4$ | 7 | 6.6 | 6.5 | 53 | 51 | 0.84 (0.80) |
| Acac | 11 | 9.2 | 10.6 | 75 | 74 | 0.58 (0.89) |
|  | 26 | 10.9 | 25.3 | 86 | 92 | 0.07 (0.92) |
| $CoFe_2O_4$ | 9 |  |  | 39 | 37 |  |
| Acac | 12 |  |  | 60 | 62 |  |

Empirical Data.

Figure 12:
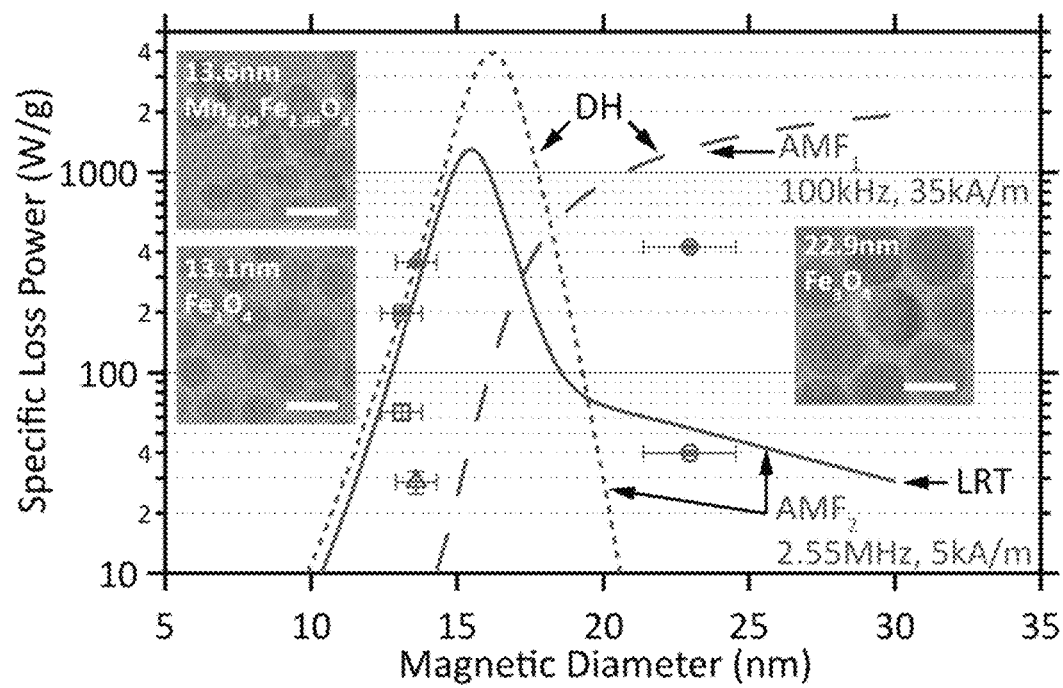
FIG. 12 provides comparison of empirical data representing the results independent magnetothermal multiplexing with the use of AMFs with different characteristics and comparison of these data with the results of calculations based on the dynamic-hysteresis approach (modified according to an embodiment of the invention) and the results of calculations based on the conventional linear response theory.

The empirical results (verifying the feasibility of the proposed independent heating of a set of magnetic particles chosen from a mix of magnetic particles with different physical properties by applying magnetic field(s) the properties of which are judiciously tailored towards magnetic activation of the chosen set(s) of particles) are shown in FIG. 12. Here, SLP values are shown for two superparamagnetic samples of $Fe_3O_4$ SDMNPs with diameters $d_m$=13.1 nm (filled squares indicate the results of exposing the particles to an AFM having a 2.55 MHz frequency and a 5 kA/m strength, "$AMF_1$"; empty squares indicate the results for an AFM having a 100 kHz frequency and a 35 kA/m strength, "$AMF_2$") and $Mn_{0.04}Fe_{2.96}O_4$ SDMNPs with $d_m$=13.6 nm (filled triangles indicate results for $AMF_1$ and empty triangles indicate results for $AMF_2$). Also shown are the results for a ferromagnetic sample of $Fe_3O_4$ SDMNPs with diameters $d_m$=22.9 nm (empty circles indicate the data obtained with $AMF_1$ and filed circles indicate data obtained with $AMF_2$). The solid line in a plot of FIG. 12 represents the results of a conventional LRT-based simulation for $Fe_3O_4$ SDMNPs of varying diameters that are driven by $AMF_1$ including Brownian relaxation. The dashed lines correspond to the simulations conducted with the used of the modified DH approach of the invention for the same SDMNPs driven by $AMF_1$ (long dash) and $AMF_2$ (short dash). TEMs of the samples are provided in inserts. Scale bars are 20 nm.

As would be appreciated by a skilled artisan based on the comparison between the theoretical and empirical data of FIG. 12, the higher amplitude mode of magnetic multiplexing method of the invention favors heat dissipation by 22.9 nm SDMNPs in the ferromagnetic regime. As anticipated, the lower amplitude mode dramatically reduces the heating of the larger SDMNPs. Increasing the frequency of the lower amplitude mode increases the Im($\chi$) of the superparamagnetic samples as compared to ferromagnetic samples, allowing them to heat more efficiently. At the same time, in the mode of activation involving the low-frequency-high-amplitude AMF, the 22.9 nm SDMNPs exhibit an SLP 6.7 times higher than the 13.1 nm samples. The application of the high-frequency-low-amplitude AFM reverses the situation, with the superparamagnetic SDMNPs exhibiting an SLP 5.0 times higher than the ferromagnetic sample. Introducing a superparamagnetic sample 13.6 nm $Mn_{0.04}Fe_{2.96}O_4$ brings these ratios to 14.9 and 8.9, respectively. Based on the bulk properties of $MnFe_2O_4$, this slight Mn doping is expected to lower SDMNPs coercivity, leading to improved performance for multiplexing. Similar strategies based on controlling composition could be applied to classes of materials with a broad range of coercivities, such as $A_xFe_{3-x}O_4$ (A=Mn, Fe, Co, Zn, Ni).

Embodiment of Biological Signaling with the Use of a Magnetically-Actuated Pyroelectric Effect.

It may be advantageous to consider alternative ways in which magnetic fields could be used to remotely generate changes in local electric fields to affect cellular targets. In nearly all of the literature on magnetoelectric (ME) composites, magnetic and electric response of a material are linked by strain as follows:

$$\begin{bmatrix} \vec{\sigma} \\ \vec{D} \\ \vec{B} \end{bmatrix} = \begin{bmatrix} \vec{\vec{C}} & \vec{\vec{e}}^T & \vec{\vec{q}}^T \\ \vec{\vec{e}} & \epsilon_0 \vec{\vec{\epsilon}} & \vec{\vec{\alpha}} \\ \vec{\vec{q}} & \vec{\vec{\alpha}}^T & \mu_0 \vec{\vec{\mu}} \end{bmatrix} \begin{bmatrix} \vec{S} \\ \vec{E} \\ \vec{H} \end{bmatrix}, \quad (5)$$

where the tensor quantities that have been introduced into the relation represent stress $\vec{\sigma}$, strain $\vec{S}$, stiffness $\vec{C}$, piezoelectric coupling $\vec{e}$, and magnetostrictive coupling $\vec{q}$ (see, for example, Nan C.-W. et al., in *J. Appl. Phys.*, 103 (3), p. 031101, 2008).

Figure 8A:
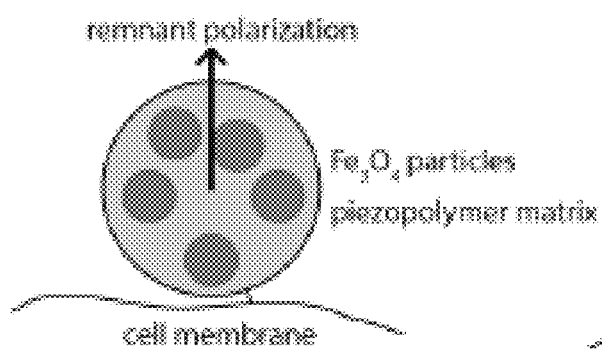
FIGS. 8A, 8B, 8C illustrate schematically a biological signaling strategy employing a magnetically actuated pyroelectric mechanism.
Figure 8B:
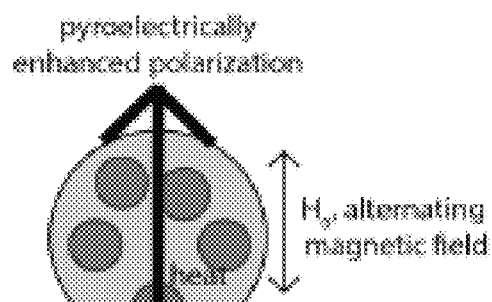
Figure 8C:
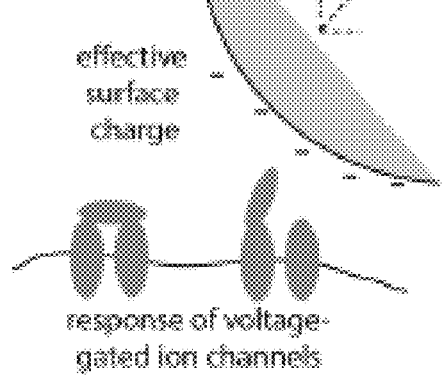

If, instead, temperature is used for mediation of the coupling between the two materials, the tensors corresponding to piezoelectric and magnetostrictive response in Eq. (5) are replaced with constants (pyroelectric and pyromagnetic constants, respectively) that describe the response of polarization and magnetization to increasing temperature. Since material-mediated biological signaling only requires the ability to influence polarization with magnetic fields, not necessarily full ME coupling, a system can be formed in which hysteretic losses of a magnetic nanoparticle heat a strongly pyroelectric material, generating a significant change in polarization therein. The heating behavior attributable to coherent magnetization reversal is likely not to be affected by the presence of the pyroelectric material and the volume of magnetic inclusions is likely not to reduce the effective surface charges realized by the pyroelectric. FIGS. 8A, 8B, and 8C provide a schematic illustration of the proposed operational scheme employing a magnetically-actuated pyroelectric-effect-based biological signaling strategy. FIG. 8A illustrates an example of the structure of one possible composite material, which involves superparamagnetic $Fe_3O_4$ particles embedded in a piezopolymer matrix. The piezopolymer (such as polyisocyante, for example) is selected preferably to have a low remnant polarization and high pyroelectric coefficient. FIG. 8B shows that an alternating magnetic field is applied to the composite particle, producing large temperature increase. FIG. 8C depicts the enhanced polarization of the particle due to the pyroelectric property of the matrix generates an action potential by biasing the voltage gated ion channels indigenous to the neuronal membrane.

In a related embodiment, this system may be alternatively realized with a polymer pyroelectric material. In particular, for a polyisocyanate having relatively low remnant polarization (16.4 mC m$^2$) and very high pyroelectric coefficient (300 microC m$^{-2}$K$^{-1}$)[26], a temperature change of 55K could nearly double its polarization from about 0.1e nm$^{-2}$ to about 0.2e nm$^{-2}$. The change in temperature in the immediate vicinity of nanoparticle(s) dissipating heat from hysteresis losses has been shown to be of this order of magnitude (Riedinger A. et al., in *Nano Letters*, 13(6), pp. 2399-2406, 2013), and could even be greater depending on the thermal conductivity of polymer and the loss power of individual nanoparticles. In one embodiment, nanoparticles may be used at low concentrations to reduce or eliminate bulk heating regardless of such large temperature change in the vicinity of the particle(s). Even if a change in polarization, resulting from the produced local heating, is below the level substantial to immediately elicit an action potential, the caused change of polarization may introduce a sufficient voltage bias to increase the probability of targeted neurons spontaneously firing. Through network interactions, this individually increased bias toward spontaneous firing could provide a way to stimulate collective activity in biological tissue while reducing the risk of overstimulation of the tissue, resulting in viable bio-therapy.

Embodiment of a Method.

Figure 9:
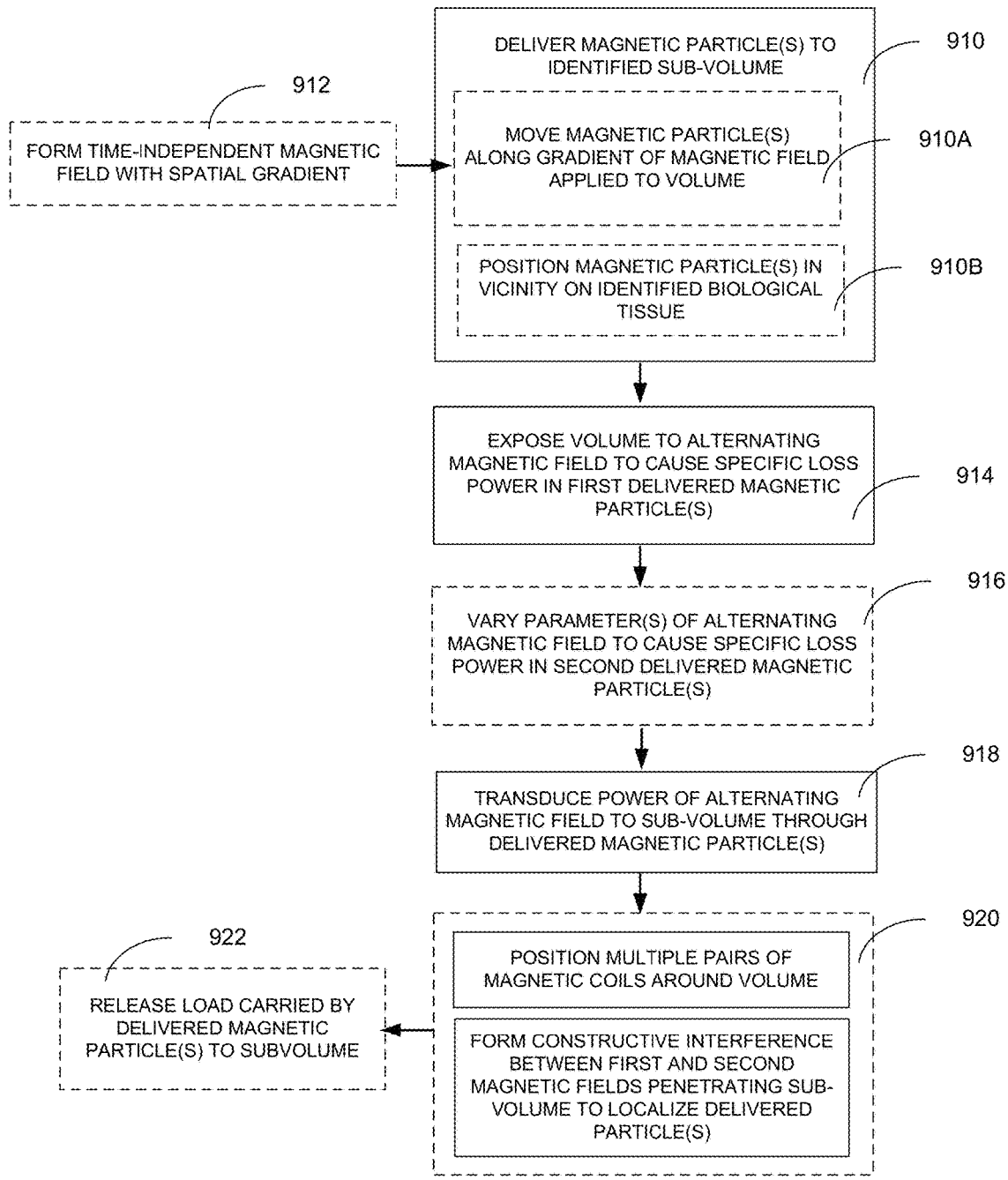
FIG. 9 is a flow-chart illustrating an embodiment of a method of the invention.

An implementation of a method for magnetically multiplexed heating of the invention, directed to selective heating of a region of interest (ROI) of a volume of a target (which, in a specific case, may be a biological tissue), is illustrated in FIG. 9. In this example, specifically configured magnetic particles (or a mix of magnetic particles of different materials and/or geometries) are introduced to an identified ROI (sub-volume) at step 910. Generally it is done by mixing the particles with the material of which the volume is being made; or, in the case of a tissue, with the use of chemical targeting or other affinity mechanism. In one specific case, such particles can be optionally delivered to the ROI with the use of time-independent magnetic field formed across the volume with a spatial gradient defined such as to propagate the magnetic particles to the ROI (910A, 912) and/or placed in the vicinity or at biological tissue at the ROI, 910B. At step 914, the volume with the ROI and magnetic particle(s) delivered to the ROI is exposed to the at least one alternating magnetic field with parameters judiciously defined to cause specific loss power in identified delivered magnetic particles (or in an identified sub-set of the mix of the delivered particles). In the process of exposure of the particles to the alternating magnetic field, parameters of such field can be optionally varied at step 916 to ensure that a different set of delivered magnetic particles is affected, at discretion of the user. Thereafter, power of the alternative magnetic field is transduced to the ROI through the identified magnetic particles exposed to the alternating magnetic field, 918. As part of the process of the power transduction to the ROI, at step 920, multiple magnetic fields may be activated to penetrate through the ROI such as to cause constructive interference of such magnetic fields to localize the magnetic particles at the spatial region defined by the interference. Alternatively or in addition, a load carried by magnetic particles exposed to the defined alternating field(s) (such as, for example, a compound affixed to the particles) is released at the ROI, at step 922.

It is understood therefore that, generally, embodiments of the invention may include the steps of delivering a magnetic particle to the sub-volume and activating an alternating magnetic field to transduce a power thereof to a sub-volume through the magnetic particle. The step of activating may include generating a magnetic field with at least one magnetic coil. In one implementation, in order to increase the field strength in the sub-volume, the magnetic field is activated by juxtaposing at least two pairs of coils with the volume such as to form, in the sub-volume, a constructive interference between magnetic fields correspondingly formed by the at least two pairs of coils and penetrating through the volume.

The step of delivering may, optionally and in a specific case, include moving a magnetic particle along a vector corresponding to spatial gradient of a magnetic field applied to the sub-volume. The step of activating may include exposing the sub-volume to the alternative magnetic field to cause a generation of specific loss power corresponding to the magnetic particle. For example, a mix of magnetic particles can be delivered to the volume such as to spatially associate the first magnetic particles with a first sub-volume of the volume and the second magnetic particles with a second sub-volume of the volume, where the mix of magnetic particles contains first magnetic particles characterized by first parameters and second magnetic particles characterized by second parameters, at least some of the first parameters being different from at least some of the second parameters. In one particular application, the step of delivering may include respectively positioning of the first and second magnetic particles in the vicinity of first and second cells of a biological tissue occupying the volume, where such first and second cells have different biological responses. The delivering includes delivering magnetic particles intermixed in a heat-conducting host material. The step of delivering may include delivering magnetic particles intermixed in a physiological fluid and/or in a heat-conducting host material It is appreciated that, according to the method, the process of multiplexing can be effectuated with respect to either SLP or IPLP (either of which is referred to as a loss power or LP), and the needs of a particular application would inform the design choices made in selecting materials.

Additionally, the method of the invention may include a step of exposing an entirety of the volume to a first alternating magnetic field having first alternating magnetic field parameters defined such as to cause a generation of a first LP associated with the first magnetic particles and a second LP associated with the second magnetic particles, the first LP being higher than the second LP. When such is the case, the formation of a time-independent field with spatial gradient throughout the volume may be used to reposition at least one of the first and second magnetic particles within the volume (towards the identified sub-volume of interest). While exposing the entirety of the volume to alternating magnetic field, the entirety of the volume can be exposed to the first alternating magnetic field having alternating magnetic field parameters defined such as to generate the first LP while leaving the second magnetic particles substantially unaffected by the alternating magnetic field.

Afterwards, a second AMF having second AMF parameters can be activated to expose the entirety of the volume to said second AMF while deactivating the first AMF and ceasing the generation of the first LP, the second AMF parameters defined such as to cause generation of the second LP at the second magnetic particles. In doing so, the first and second alternative magnetic fields may be optionally configured such that a first figure of merit defined by a product of an amplitude and frequency of the first alternating magnetic field substantially equals to a second figure of merit defined by a product of an amplitude and frequency of the second alternating magnetic field. An embodiment of the method may additionally include a step of releasing at least one compound associated with at least one of the first and second magnetic particles to volume in response to the act of activating a magnetic field.

It is also appreciated that, in a specific case, a method of the invention may be directed to multi-modal magnetic stimulation (magnetically multiplexed stimulation) of a region of interest (ROI) of a volume of a biological tissue. Such method includes (i) delivering first and second magnetic particles to the ROI; and (ii) forming alternating magnetic field across the ROI, the alternating magnetic field having alternating magnetic field parameters defined to selectively heat the first magnetic particles while leaving the second magnetic particles substantially unaffected by the alternating magnetic field. The step of delivering may include delivering magnetic particles dimensioned to generate a LP characterizing the magnetic particles in response to exposing the magnetic particles to the alternating magnetic field. (In one case, the delivering may includes delivering magnetic particles characterized by respectively corresponding single magnetic domains.)

The method may further include a step of changing parameters of the alternating magnetic field to initiate selective heating of the second magnetic particles while substantially ceasing selective heating of the first magnetic particles. In the process of delivering the particles to the ROI, the first magnetic particles may be adhered to first cells of the ROI and the second magnetic particles may be adhered to second cells in the ROI (the first and second cells are such that they are associated with different biological cascades). Parameters of the alternating magnetic field may be varied from the first parameters to the second parameters to maintain substantially constant a figure of merit that is defined by a product of amplitude and frequency of the alternating magnetic field.

Modifications to, and variations of, the illustrated embodiments and practical applications of such embodiments may be made without departing from the inventive concepts disclosed above.

For example, in one case an embodiment of the disclosed invention can be advantageously employed to effectuate a magnetically multiplexed release of payloads (such as pharmacological compounds, synthetic biological signaling molecules: neurotransmitters, hormones, etc.) in circulating physiological fluids (such as blood and cerebro-spinal fluid, CSF), thereby implementing a bio-switch.

An embodiment of the present invention makes it possible to garnish different cell types with magnetic particles tuned to AFMs with different parameters, thereby allowing for independent activation of ensembles of identified cells even if the cells are in proximity to one another. Such a technique allows one to study the roles of cell populations in physiological processes, in particular those functions that are, or would be, perturbed by invasive methods. In a practical situation when a mix of MNPs (containing subpopulations of MNPs characterized by pre-determined hysteretic losses that differ from sub-population to subpopulation) is associated with the biological tissue, a typical amplitude of the AMF used to effectuate multi-modal magnetic stimulation of the tissue and implement a bio-switch may be on the order of 10 mT or less, while the typical range of frequencies is between about 10 kHz and 50 MHz. For example, when the first sub-population of the MNPs associated with the excitatory cells of the tissue and the second sub-population of the MNPs is associated with the inhibitor cells, the activation and de-activation of heat dissipation in one of such sub-populations carried out independently and without interference with another sub-population allows for independent triggering of responses of excitatory and inhibitor cells. In a related embodiment, where the first group of cells (for example, brain cells) releases a compound neurotransmitter such as, for example, dopamine and the second group of brain cells releases serotonin, the independent activation and deactivation of the first and second groups of brain cells via M3S of the respectively associated MNPs (for example, in a fashion described in reference to FIGS. 3A, 3B) results in implementation of a brain-stimulator device.

As an example of the specific context, distinct chemical payloads can be specifically attached to the magnetic nanoparticles MNPs of differing compositions and/or sizes with the use of thermally-responsive organic linkages (such as azo-based linkers and nucleic acids, for example). Then, such distinct payloads are independently released from different MNPs (that have been introduced aggregately or separately into the blood stream or other circulating physiological fluid) in different locations in the body with the use of alternating magnetic fields having different characteristics, according to an embodiment of the invention. Spatial guidance of the MNPs with magnetic fields can be used, as discussed above, to temporary localize MNPs in an organ of interest. Examples of such use of an embodiment of the invention may include release of multiple pharmacological compounds targeting different organs following a single injection into the blood stream. Similarly, a single injection of an MNP cocktail into the CSF may allow release of several compounds (e.g. neuromodulators, growth factors, synthetic neurotransmitters) in several different locations (with special precision of down to 0.5 mm) in the nervous system independently with differing conditions of AMF applied externally and broadly. Table 2 provides examples of practical applications of payload release effectuated according to an embodiment of the invention.

as a result of local heating in the presence of an AMF. Magnetic multiplexing would therefore offer the possibility of multiple-stage release of a chosen drug and/or independent control over the release of multiple drugs.

In another example, magnetically multiplexed targeting and release of cells in the blood can be effectuated with the use of an embodiment of the invention. If cells are captured in the blood through chemical affinity to functionalized MNPs, magnetothermal multiplexing can be used to preferentially release them for sorting and manipulation. Specifically, a mixture of MNPs decorated with thermally-responsive targeting moieties (e.g. antibodies, folic acid, viral recognition domains etc. conjugated to thermally responsive linkers) can be injected into the blood where they will preferentially attach to their targets (e.g. specific cell-types, infected blood cells, cancer cells, bacteria, parasites). The blood sample can be then subjected to a series of differently-conditioned magnetic fields, each exposure caus-

TABLE 2

| Payload Type | Tissue/organ | Application(s) of Multiplexing |
| --- | --- | --- |
| Synthetic Neurotransmitters | Brain | Independent release of different neurotransmitters and/or neuromodulators and/or growth and regeneration factors in the same brain structure |
| Neuromodulators | | Independent chemical stimulation of different brain structures despite their close spatial proximity. |
| Growth and regeneration factors | | Independent chemical stimulation of distinct cell populations despite their close spatial proximity. (Compounds are tethered to the MNP surfaces and are exposed to receptors upon AMF-induced heating via conformational changes in organic ligands on MNP surfaces) |
| Anti-cancer drug | Tumors | Suppose that two different tumors require different types of anticancer drugs and that the drugs are active only after release from the surface of the nanoparticles. Multiplexing in this case would allow for site specific independent dosing of each tumor following a global injection and magnetically assisted accumulation in both tumors.<br>Sequential delivery of multiple drugs to a tumor, i.e. lets suppose that several drugs need to be released within the same tumor in specific temporal sequence. We can accomplish this by tethering these drugs to different MNPs and orchestrating sequential release via precisely timed application of different AMF conditions |
| Hormonal regulation | E.g. kidney, liver | Supposing that a therapy utilized the release of hormones or growth factors within these organs, site specific and temporally distinct control over the release of these substances would be possible with multiplexing. |

Figure 13C:
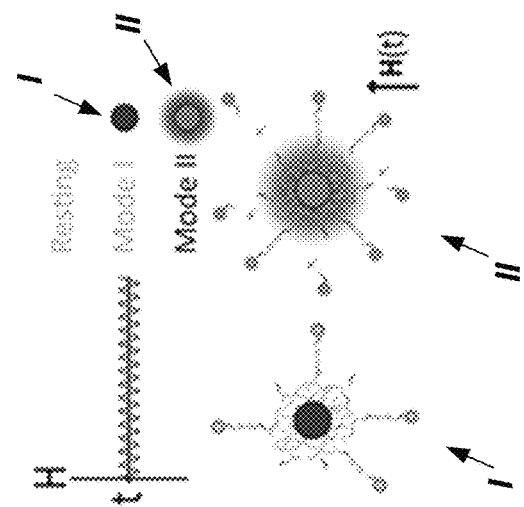
FIGS. 13A, 13B, 13C provide illustrations to the example of a therapeutic application (thermally activated drug release) enhanced with the use of an embodiment of the invention. Drugs are shown be attached to magnetic nanoparticles with thermally labile bonds that break as a result of local heating in the presence of an AMF.
Figure 13B:
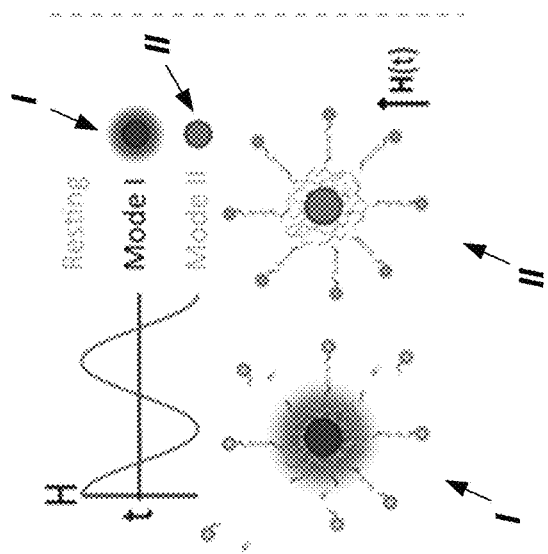
Figure 13A:
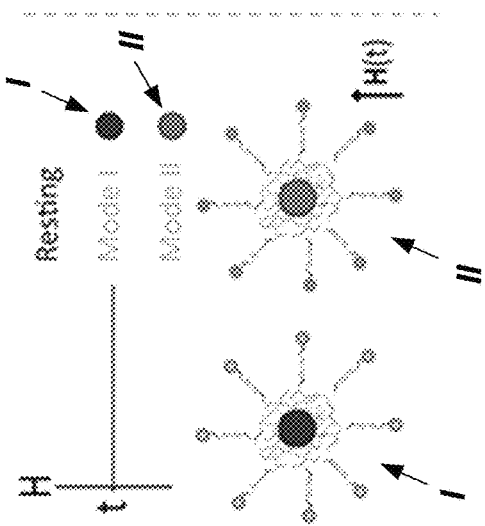

FIGS. 13A, 13B, 13C illustrate schematically an example of a therapeutic application that could be enhanced by magnetothermal multiplexing is thermally activated drug release. Here, FIG. 13A provides illustration to a resting condition, FIG. 13B shows the payload-release due to the magnetic activation in "mode I", and FIG. 13B illustrates the payload-release due to magnetic activation in "mode II". Drugs can be attached with thermally labile bonds that break ing a release of a specific target (e.g. cell, parasite) for further investigation. Similarly, the application of AMFs with different field properties conditions can be used for blood purification from complex parasites. Specific applications may include profiling of cancers, removal of multiple parasites. Table 3 provides examples of practical applications of magnetically multiplexed heating for targeted capture and release.

TABLE 3

| Targeted Organism/Cell Type | Benefit of Controlled Release via Multiplexing According to Embodiment of the Invention |
| --- | --- |
| Cancer cells | Different types of MNPs capable of multiplexing could be functionalized to bind to different cancer cell types. Subsequent to chemical binding and magnetic separation from the blood, heating via AMF could release cells back into solution in vitro. Different types of cancer cells could be sorted for further study by selective release from the bound nanoparticles accomplished via magnetothermal multiplexing. |

TABLE 3-continued

| Targeted Organism/Cell Type | Benefit of Controlled Release via Multiplexing According to Embodiment of the Invention |
|---|---|
| Parasites | The mechanism is analogous to the previous example, except in this case applied to multicellular organisms. |

Accordingly, an embodiment of the method may include a step of delivering the mix of particles to the corresponding sub-volumes of the volume that includes respectively associating the first and second magnetic particles (each of which is equipped with a corresponding thermally-responsive moiety) with the first and second cells in blood stream of a biological tissue, the first and second cells characterized by different biological responses, and step of releasing of at least one of the first and second cells for identification of said responses.

FIGS. 14A, 14B, 14C illustrate schematically a therapeutic process employing SDMNPs and their coupling to temperature-sensitive cellular structures 1410, 1420 in order to provide a mechanism for supplying stimulus minimally invasively. Here, FIG. 14A provides illustration to a resting condition, FIG. 14B shows the targeted capture/release due to the magnetic activation in "mode I", and FIG. 14B illustrates the targeted capture/release due to magnetic activation in "mode II". With targeting, the multiplexing effectuated according to an embodiment of the invention allows for independent stimulation of different cell types, even for those in close proximity of one another.

In yet another application, an embodiment of the invention may be used to effectuate magnetically multiplexed heat-based biological stimulation. Multiplexing with MNPs can be used to remotely stimulate specific neural populations even if they are co-located in a given volume. Specifically, MNPs of differing composition and/or sizes can be targeted to specific neuronal types in specific locations (axons, cell bodies, synapses). Neural activity can be modulated through naturally occurring thermally responsive ion channels (for example, calcium channels TRPV1, 2, 3, TRPA1; potassium channel TREK1) as well as the thermally evoked change in membrane capacitance. In particular, TRPV channels can be controlled with heat from MNPs to evoke neural activity, while TREK channels have been implicated as heat-mediated transducers of neuronal inhibition. Consequently, by coupling differing MNP types to different channels on different cells we can control neuronal activity with differing AMF conditions. Specific applications may include targeting different MNPs to different fibers within peripheral nerves for remote modulation of internal organ function. Multiple MNP types can be used for precise control of firing patterns of specific fibers innervating the organs such as heart, liver, kidneys and stomach. Alternatively different MNPs can be targeted to different plexi at specific organs and independent neuromodulation can be orchestrated between different organs. AMFs can penetrate deeply into the biological tissues making this method for more suitable to peripheral nerve modulation as compared to other minimally invasive alternatives. Table 4 provides examples of practical applications of magnetically multiplexed heat-based biological stimulation.

TABLE 4

| Example of structures | Use of multiplexing | Implementation |
|---|---|---|
| Brain | Addressing structures in close proximity | While brain structure A is stimulated to treat symptoms of disease X, brain structure B is stimulated to treat symptoms of disease Y, etc. Magnetothermal multiplexing enables independent stimulation of these structures, despite close proximity so that a patient with multiple neurological diseases can be separately treated for each one separately. |
| Brain | Addressing different cell types within the same structure | When different MNPs are associated with different cells types (e.g. excitatory or inhibitory neurons) within the same brain structure, magnetothermal multiplexing causes selective stimulation of each type, eliciting a different therapeutic response. |
| Brain | Developing stimulation sequences relying on temporally separated stimulation of different cell types or structures | The ability to selectively and independently stimulate different cell types and different brain structures with high spatial specificity defines a new class of therapies relying upon the effects of stimulation sequences. Varying the order, duration, and intensity of simulation could offer benefits different from selectively stimulating any single structure or cell type alone. |

Accordingly, an embodiment of the method may include a step of remotely stimulating co-located neural populations in the region of interest of the brain.

Furthermore, magnetothermal multiplexing approach configured according to an embodiment of the invention can be used for mechanical actuation of a portion of or a whole device. In instances (where the heating of magnetic nanoparticles triggers a mechanical response from a material, including but not limited to incorporation into shape memory polymer composites, magnetothermal multiplexing offers novel functionalities). This can come in the form of either a) multistage magnetic actuation of a single structure or b) independent actuation of separate structures in close proximity. Shape-memory polymer-based devices could be fabricated, for example, through multi-material 3D printing techniques to produce arbitrary geometries of shape memory polymers actuated with mild heat, e.g. acting as stents, drug release devices, etc. The ability to selectively trigger the shape memory of different parts of a structure at different points in time offered by magnetothermal multiplexing opens a broad and nuanced design space for responsive devices. The proposed devices and their operation may involve both-path independent and path-dependent responses to magnetothermal inclence, with a simple 2D illustration of the concept shown in FIGS. 15A, 15B.

Figure 15A:
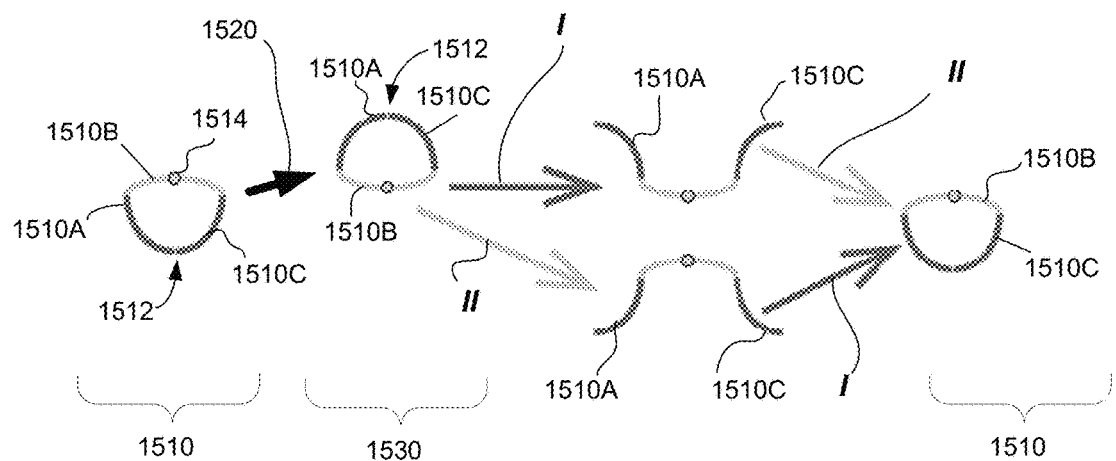
FIGS. 15A and 15B illustrate mechanical activation of a shape-memory polymer based device complemented with MNPs, caused by transduction of power of an alternating magnetic field to the portions of the device according to an embodiment of the invention.

FIG. 15A shows an example of a geometry where the order in which the segments are heated does not affect the final shape. The simplified example of the device 1710 includes three portions 1510A, 1510B, 1510C made of a shape-memory polymer embedding MNPs configured for magnetothermal multiplexing. The portion 1510A is connected to the portion 1510B, and the portion 1510B is extended by the portion 1510C; all three forming a longitudinally-uninterrupted unit shaped/bend as an open loop such as to leave a gap 1512 between the free ends of the portions 1510A, 1510C. The "circle" 1514 denotes a spatial "anchor", at which the embodiment 1510 is fixed in space. In this simple example, the initial structure 1510 is heated and each segment is bent so that its curvature is inverted. Upon cooling, the structure retains this configuration. When in the body, a mild temperature increase accomplished via heat released by embedded MNPs, triggering the shape memory response to that the segment returns to its original configuration. At least one of the portions (and in a specific case—all three portions) includes judiciously chosen magnetic particles embedded therein (not shown). Due to heat treatment 1520 of the whole device (caused by specific loss power in magnetic particles embedded in the portions 1510A, 1510B, 1510C exposed to the appropriately chosen alternating magnetic field, as discussed above, and followed by the cooling of the device), the arms 1510A, 1510C of the device 1510 are "flexed" such as to cause a change of shape of the device from 1510 to 1530. At this point, regardless of which path of heat treatment is chosen—whether the first path (including the heat treatment I of the portions 1510, 1510C only followed by the heat treatment II of the portion 1510B only) or the second path (including the heat treatment II of the portion 1510B only followed by the heat treatment I of the portions 1510A, 1510C only), the shape of the device is returned to the original shape 1510.

Figure 15B:
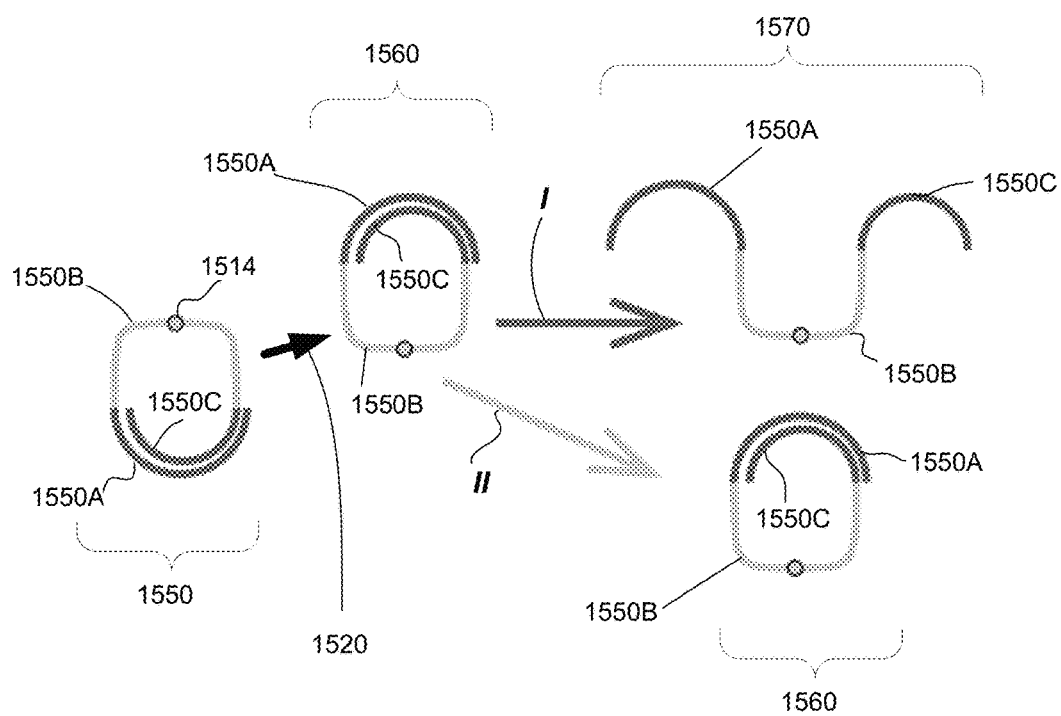

FIG. 15B illustrates a path-dependent shape memory response caused by magnetothermal multiplexing of an embodiment of the invention. In the example of the device 1550, having three portions 1550A, 1550B, 1550C longitudinally-extending each other to form an uninterrupted unit shaped as a spiral, the differently configured heat-treatment of different parts of the device results in different final shapes (in other words, the performance of the device depends on the path of heat-treatment). As would be understood by a person of the skill in the art, the difference between the magnetothermal process driven operation of the devices 1510 and 1550 is explained by spatial coordination of the portions of the devices. Specifically, due to heat treatment 1520 of the whole device (caused by specific loss power in magnetic particles embedded in the portions 1550A, 1550B, 1550C exposed to the appropriately chosen alternating magnetic field, as discussed above, and followed by the cooling of the device), the arms 1550A, 1550C of the device 1510 are "flexed" such as to cause a change of shape of the device from 1550 to 1560. Starting at this point, however, and depending on the path of the heat treatment I or II, the resulting shapes of the device will differ: when only the end portions 1550A, 1550C are heated using the method of the invention, the resulting shape is that shown as 1570.

However, when only the central portion 1550B is heated (path II), no change of the shape occurs due to mechanical "interlocking" of the portions 1550A, 1550C with one another, and the device remains shaped as 1560.

Accordingly, an embodiment of the method of the invention may include steps of varying the AMF applied to the region of interest of the biological tissue by changing the first AMF parameters to second AMF parameters, and changing a shape of a unit containing a shape-memory polymer in response to said varying (said unit having been placed at the ROI).

Embodiments of the invention also lend themselves to governing magnetothermal multiplexing for triggering changes in electrical polarization. The pyroelectric effect is utilized to couple the heating of a material to changes in its electric polarization. By incorporating magnetic nanoparticles into a composite with a high pyroelectric coefficient, it may be possible to control a structure's (element's) polarization with the heat dissipated in an alternating magnetic field. (Examples of pyroelectric materials include, but are not limited to, $BaTiO_3$, $LiTaO_3$, and various polymers including polyvinylidene fluoride.) This change in electric polarization could be used for biomedical aims, for instance by triggering voltage gated ion channels or controllably altering the interaction of a particle with the biological milieu or cellular structures in order to facilitate a therapeutic action. Magnetothermal multiplexing makes possible the temporally independent control of several structures or subpopulations of structures in close spatial proximity. Accordingly, an embodiment of the method of the invention may include a step of changing polarization characteristic of an element at the ROI.

Another application of embodiments of the present invention may be directed to repeated use of magnetic hyperthermia without side effects caused by heating the MNPs already present in the target. Magnetic hyperthermia is designed to ablate cancerous tissue using the heat dissipated by magnetic nanoparticles, either alone or in combination with anticancer drugs. If the treatment is successful, the patient is left with a residue of ferrofluid in now healthy tissue. Without magnetothermal multiplexing, the recurrence of cancer with the formation of a tumor in close proximity to the original ferrofluid residue could preclude the possibility repeating the treatment. With magnetothermal multiplexing, different material types could be used for each injection, and they could be heated with different alternating magnetic field conditions. The approach configured according to an embodiment of the present invention allows to avoid the danger of damaging the healthy tissue surrounding the MNPs already present in the body.

Some steps of the process of multimodal magnetic heating and/or the process of multimodal magnetic stimulation of the tissue, as described above, may require the employment of a programmable electronic circuitry (such as a computer processor) controlled by instructions stored in a memory). The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, it is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The invention as recited in claims appended to this disclosure is intended to be assessed in light of the disclosure as a whole. Disclosed aspects, or portions of these aspects, may be combined in ways not listed above. Accordingly, the invention should not be viewed as being limited to the disclosed embodiment(s).

What is claimed is:

1. A method for magnetically-multiplexed stimulation of a region of interest (ROI) of a volume of a target, the method comprising:
   delivering first and second magnetic particles to the ROI of a biological tissue of the target,
   wherein the delivering includes delivering the first magnetic particles to a first neural population of a brain and delivering the second magnetic particles to a second neural population of the brain;
   forming an alternating magnetic field (AMF) across the ROI, the AMF having first AMF parameters defined to selectively heat the first magnetic particles while leaving the second magnetic particles substantially unaffected by the AMF;
   changing the first AMF parameters of the AMF to initiate selective heating of the second magnetic particles while substantially ceasing selective heating of the first magnetic particles; and
   independently invoking neural activity in said first and second neural populations with the use of said AMF.

2. A method according to claim 1, wherein the delivering includes delivering magnetic particles, from the first and second magnetic particles, further comprising exposing said magnetic particles to the alternating magnetic field, wherein at least one of dimensions, shapes, and compositions of said magnetic particles is configured to generate, in response to said exposing, a loss power characterizing said magnetic particles.

3. A method according to claim 2, further comprising
   varying the AMF by changing the first AMF parameters to second AMF parameters, and
   changing a shape of a unit containing a shape-memory polymer in response to said varying, said unit having been placed at the ROI.

4. A method according to claim 2, further comprising changing a polarization characteristic of an element at the ROI.

5. A method according to claim 1, wherein the delivering includes adhering the first magnetic particles to first cells of the ROI and further includes adhering the second magnetic particles to second cells in the ROI, the first and second cells associated with different biological cascades.

6. A method according to claim 5, further comprising changing the first AMF parameters of the AMF to second AFM parameters defined to maintain substantially constant a figure of merit that is defined by a product of amplitude and frequency of the AFM.

7. A method according to claim 1, wherein the delivering include respectively positioning the first and second magnetic particles in a vicinity of first and second.

8. A method according to claim 1, further comprising independently releasing at least one of first and second chemical payloads respectively associated with the first and second magnetic particles in response to said forming and said changing.

9. A method according to claim 1, wherein the delivering includes delivering the first and second magnetic particles intermixed in a heat-conducting host material.

* * * * *